United States Patent
Yan et al.

(10) Patent No.: US 7,077,860 B2
(45) Date of Patent: Jul. 18, 2006

(54) METHOD OF REDUCING OR ELIMINATING THROMBUS FORMATION

(75) Inventors: John Y. Yan, Los Gatos, CA (US); Randy Chan, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 10/877,527

(22) Filed: Jun. 24, 2004

(65) Prior Publication Data

US 2004/0236417 A1    Nov. 25, 2004

Related U.S. Application Data

(62) Division of application No. 08/847,763, filed on Apr. 24, 1997, now Pat. No. 6,776,792.

(51) Int. Cl.
 *A61F 2/06* (2006.01)
(52) U.S. Cl. .................. 623/1.15; 623/1.43; 623/921; 427/2.25
(58) Field of Classification Search ............... 623/1.43, 623/1.46, 23.71, 1.15, 920, 921; 427/2.25
See application file for complete search history.

(56) References Cited

U.S. PATENT DOCUMENTS

| | | | |
|---|---|---|---|
| 2,072,303 A | 3/1937 | Herrmann et al. | |
| 2,386,454 A | 10/1945 | Frosch et al. | |
| 2,647,017 A | 7/1953 | Coulliette | |
| 2,701,559 A | 2/1955 | Cooper | |
| 3,288,728 A | 11/1966 | Gorham | |
| 3,687,135 A | 8/1972 | Stroganov et al. | |
| 3,773,737 A | 11/1973 | Goodman et al. | |
| 3,839,743 A | 10/1974 | Schwarcz | |
| 3,849,514 A | 11/1974 | Gray, Jr. et al. | |
| 3,900,632 A | 8/1975 | Robinson | |
| 4,075,045 A | 2/1978 | Rideout | |
| 4,104,410 A | 8/1978 | Malecki | |
| 4,110,497 A | 8/1978 | Hoel | |
| 4,132,357 A | 1/1979 | Blackinton | |
| 4,164,524 A * | 8/1979 | Ward et al. .................. | 264/39 |
| 4,226,243 A | 10/1980 | Shalaby et al. | |
| 4,321,711 A | 3/1982 | Mano | |
| 4,323,071 A | 4/1982 | Simpson et al. | |
| 4,329,383 A | 5/1982 | Joh | |
| 4,338,942 A | 7/1982 | Fogarty | |
| 4,343,931 A | 8/1982 | Barrows | |
| 4,346,028 A | 8/1982 | Griffith | |

(Continued)

FOREIGN PATENT DOCUMENTS

CA    2 008 312    7/1990

(Continued)

OTHER PUBLICATIONS

U.S. Appl. No. 10/255,913, filed Sep. 26, 2002, Tang et al.

(Continued)

*Primary Examiner*—Paul B. Prebilic
(74) *Attorney, Agent, or Firm*—Squire, Sanders & Dempsey L.L.P.

(57) ABSTRACT

An implantable stent is coated with a material that attracts heparin and with which heparin forms a bond. The stent is exposed to a heparin containing solution just prior to implantation or is first implanted and then exposed to heparinized blood. As heparin becomes detached from the stent, the implantation site is exposed to heparin to restore an effective level and thereby prevent thrombosis.

20 Claims, 1 Drawing Sheet

U.S. PATENT DOCUMENTS

| | | |
|---|---|---|
| 4,439,185 A | 3/1984 | Lundquist |
| 4,489,670 A | 12/1984 | Mosser et al. |
| 4,516,972 A | 5/1985 | Samson et al. |
| 4,529,792 A | 7/1985 | Barrows |
| 4,538,622 A | 9/1985 | Samson et al. |
| 4,554,929 A | 11/1985 | Samson et al. |
| 4,573,470 A | 3/1986 | Samson et al. |
| 4,596,574 A | 6/1986 | Urist |
| 4,599,085 A | 7/1986 | Riess et al. |
| 4,608,984 A | 9/1986 | Fogarty |
| 4,611,051 A | 9/1986 | Hayes et al. |
| 4,612,009 A | 9/1986 | Drobnik et al. |
| 4,616,593 A | 10/1986 | Kawamura et al. |
| 4,616,652 A | 10/1986 | Simpson |
| 4,629,563 A | 12/1986 | Wrasidlo |
| 4,633,873 A | 1/1987 | Dumican et al. |
| 4,638,805 A | 1/1987 | Powell |
| 4,656,083 A | 4/1987 | Hoffman et al. |
| 4,656,242 A | 4/1987 | Swan et al. |
| 4,699,611 A | 10/1987 | Bowden |
| 4,702,252 A | 10/1987 | Brooks et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,748,982 A | 6/1988 | Horzewski et al. |
| 4,768,507 A | 9/1988 | Fischell et al. |
| 4,774,039 A | 9/1988 | Wrasidlo |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,828,561 A | 5/1989 | Woodroof |
| 4,850,999 A | 7/1989 | Planck |
| 4,865,870 A * | 9/1989 | Hu et al. .................. 427/2.1 |
| 4,871,542 A | 10/1989 | Vilhardt |
| 4,877,030 A | 10/1989 | Beck et al. |
| 4,878,906 A | 11/1989 | Lindemann et al. |
| 4,879,135 A | 11/1989 | Greco et al. |
| 4,880,683 A | 11/1989 | Stow |
| 4,882,168 A | 11/1989 | Casey et al. |
| 4,886,062 A | 12/1989 | Wiktor |
| 4,902,289 A | 2/1990 | Yannas |
| 4,906,423 A | 3/1990 | Frisch |
| 4,931,287 A | 6/1990 | Bae et al. |
| 4,932,353 A | 6/1990 | Kawata et al. |
| 4,941,870 A | 7/1990 | Okada et al. |
| 4,943,346 A | 7/1990 | Mattelin |
| 4,950,227 A | 8/1990 | Savin et al. |
| 4,955,899 A | 9/1990 | Della Corna et al. |
| 4,967,606 A | 11/1990 | Wells et al. |
| 4,977,901 A | 12/1990 | Ofstead |
| 4,988,356 A | 1/1991 | Crittenden et al. |
| 4,994,033 A | 2/1991 | Shockey et al. |
| 4,994,298 A | 2/1991 | Yasuda |
| 4,994,560 A | 2/1991 | Kruper, Jr. et al. |
| 5,015,505 A | 5/1991 | Cetnar |
| 5,019,090 A | 5/1991 | Pinchuk |
| 5,019,096 A | 5/1991 | Fox, Jr. et al. |
| 5,028,597 A | 7/1991 | Kodama et al. |
| 5,037,392 A | 8/1991 | Hillstead |
| 5,037,427 A | 8/1991 | Harada et al. |
| 5,040,548 A | 8/1991 | Yock |
| 5,047,050 A | 9/1991 | Arpesani |
| 5,049,132 A | 9/1991 | Shaffer et al. |
| 5,053,048 A * | 10/1991 | Pinchuk .................. 623/1.43 |
| 5,059,166 A | 10/1991 | Fischell |
| 5,059,169 A | 10/1991 | Zilber |
| 5,059,211 A | 10/1991 | Stack et al. |
| 5,062,829 A | 11/1991 | Pryor et al. |
| 5,064,435 A | 11/1991 | Porter |
| 5,078,720 A | 1/1992 | Burton et al. |
| 5,081,394 A | 1/1992 | Morishita et al. |
| 5,084,065 A | 1/1992 | Weldon et al. |
| 5,085,629 A | 2/1992 | Goldberg et al. |
| 5,087,244 A | 2/1992 | Wolinsky et al. |
| 5,087,394 A | 2/1992 | Keith |
| 5,100,429 A | 3/1992 | Sinofsky et al. |
| 5,100,992 A | 3/1992 | Cohn et al. |
| 5,102,402 A | 4/1992 | Dror et al. |
| 5,104,410 A | 4/1992 | Chowdhary |
| 5,108,416 A | 4/1992 | Ryan et al. |
| 5,108,417 A | 4/1992 | Sawyer |
| 5,108,755 A | 4/1992 | Daniels et al. |
| 5,112,457 A | 5/1992 | Marchant |
| 5,116,318 A | 5/1992 | Hillstead |
| 5,116,365 A | 5/1992 | Hillstead |
| 5,123,917 A | 6/1992 | Lee |
| 5,127,362 A | 7/1992 | Iwatsu et al. |
| 5,133,742 A | 7/1992 | Pinchuk |
| 5,134,192 A | 7/1992 | Feijen et al. |
| 5,147,370 A | 9/1992 | McNamara et al. |
| 5,156,623 A | 10/1992 | Hakamatsuka et al. |
| 5,156,911 A | 10/1992 | Stewart |
| 5,158,548 A | 10/1992 | Lau et al. |
| 5,163,951 A | 11/1992 | Pinchuk et al. |
| 5,163,952 A | 11/1992 | Froix |
| 5,163,958 A | 11/1992 | Pinchuk |
| 5,165,919 A | 11/1992 | Sasaki et al. |
| 5,167,614 A | 12/1992 | Tessmann et al. |
| 5,171,445 A | 12/1992 | Zepf |
| 5,176,638 A | 1/1993 | Don Michael |
| 5,188,734 A | 2/1993 | Zepf |
| 5,192,311 A | 3/1993 | King et al. |
| 5,197,977 A | 3/1993 | Hoffman, Jr. et al. |
| 5,205,822 A | 4/1993 | Johnson et al. |
| 5,213,561 A | 5/1993 | Weinstein et al. |
| 5,213,576 A | 5/1993 | Abiuso et al. |
| 5,219,980 A | 6/1993 | Swidler |
| 5,222,971 A | 6/1993 | Willard et al. |
| 5,225,750 A | 7/1993 | Higuchi et al. |
| 5,226,889 A | 7/1993 | Sheiban |
| 5,226,913 A | 7/1993 | Pinchuk |
| 5,229,045 A | 7/1993 | Soldani |
| 5,229,172 A | 7/1993 | Cahalan et al. |
| 5,232,444 A | 8/1993 | Just et al. |
| 5,234,456 A | 8/1993 | Silvestrini |
| 5,234,457 A | 8/1993 | Andersen |
| 5,236,447 A | 8/1993 | Kubo et al. |
| 5,242,399 A | 9/1993 | Lau et al. |
| 5,254,089 A | 10/1993 | Wang |
| 5,254,091 A | 10/1993 | Aliahmad et al. |
| 5,258,020 A | 11/1993 | Froix |
| 5,258,419 A | 11/1993 | Rolando et al. |
| 5,269,802 A | 12/1993 | Garber |
| 5,272,012 A | 12/1993 | Opolski |
| 5,278,200 A | 1/1994 | Coury et al. |
| 5,279,594 A | 1/1994 | Jackson |
| 5,282,823 A | 2/1994 | Schwartz et al. |
| 5,282,860 A | 2/1994 | Matsuno et al. |
| 5,286,254 A | 2/1994 | Shapland et al. |
| 5,289,831 A | 3/1994 | Bosley |
| 5,290,271 A | 3/1994 | Jernberg |
| 5,292,516 A | 3/1994 | Viegas et al. |
| 5,298,260 A | 3/1994 | Viegas et al. |
| 5,300,295 A | 4/1994 | Viegas et al. |
| 5,304,200 A | 4/1994 | Spaulding |
| 5,306,250 A | 4/1994 | March et al. |
| 5,306,286 A | 4/1994 | Stack et al. |
| 5,306,294 A | 4/1994 | Winston et al. |

| | | | | | | |
|---|---|---|---|---|---|---|
| 5,306,501 A | 4/1994 | Viegas et al. | | 5,545,208 A * | 8/1996 | Wolff et al. ............... 623/1.22 |
| 5,306,786 A | 4/1994 | Moens et al. | | 5,545,209 A | 8/1996 | Roberts et al. |
| 5,308,641 A | 5/1994 | Cahalan et al. | | 5,545,408 A | 8/1996 | Trigg et al. |
| 5,314,472 A | 5/1994 | Fontaine | | 5,551,954 A | 9/1996 | Buscemi et al. |
| 5,318,531 A | 6/1994 | Leone | | 5,554,120 A | 9/1996 | Chen et al. |
| 5,328,471 A | 7/1994 | Slepian | | 5,554,182 A | 9/1996 | Dinh et al. |
| 5,330,500 A | 7/1994 | Song | | 5,556,413 A | 9/1996 | Lam |
| 5,330,768 A | 7/1994 | Park et al. | | 5,558,642 A | 9/1996 | Schweich, Jr. et al. |
| 5,336,518 A | 8/1994 | Narayanan et al. | | 5,562,728 A | 10/1996 | Lazarus et al. |
| 5,342,283 A | 8/1994 | Good | | 5,569,463 A | 10/1996 | Helmus et al. |
| 5,342,348 A | 8/1994 | Kaplan | | 5,571,135 A | 11/1996 | Fraser et al. |
| 5,342,395 A | 8/1994 | Jarrett et al. | | 5,571,166 A | 11/1996 | Dinh et al. |
| 5,342,621 A | 8/1994 | Eury | | 5,571,567 A | 11/1996 | Shah |
| 5,344,426 A | 9/1994 | Lau et al. | | 5,578,046 A | 11/1996 | Liu et al. |
| 5,344,455 A | 9/1994 | Keogh et al. | | 5,578,073 A | 11/1996 | Haimovich et al. |
| 5,350,800 A | 9/1994 | Verhoeven et al. | | 5,584,877 A | 12/1996 | Miyake et al. |
| 5,356,433 A | 10/1994 | Rowland et al. | | 5,588,962 A * | 12/1996 | Nicholas et al. ............ 604/507 |
| 5,360,401 A | 11/1994 | Turnland et al. | | 5,591,199 A | 1/1997 | Porter et al. |
| 5,360,443 A | 11/1994 | Barone et al. | | 5,591,224 A | 1/1997 | Schwartz et al. |
| 5,364,354 A | 11/1994 | Walker et al. | | 5,591,227 A | 1/1997 | Dinh et al. |
| 5,366,504 A | 11/1994 | Andersen et al. | | 5,591,607 A | 1/1997 | Gryaznov et al. |
| 5,368,560 A | 11/1994 | Rambo et al. | | 5,593,403 A | 1/1997 | Buscemi |
| 5,370,684 A | 12/1994 | Vallana et al. | | 5,593,434 A | 1/1997 | Williams |
| 5,380,299 A | 1/1995 | Fearnot et al. | | 5,595,722 A | 1/1997 | Grainger et al. |
| 5,383,925 A | 1/1995 | Schmitt | | 5,599,301 A | 2/1997 | Jacobs et al. |
| 5,383,927 A * | 1/1995 | De Goicoechea et al. . 623/1.43 | | 5,599,307 A | 2/1997 | Bacher et al. |
| 5,385,580 A | 1/1995 | Schmitt | | 5,599,352 A | 2/1997 | Dinh et al. |
| 5,387,450 A | 2/1995 | Stewart | | 5,599,922 A | 2/1997 | Gryaznov et al. |
| 5,389,106 A | 2/1995 | Tower | | 5,605,696 A | 2/1997 | Eury et al. |
| 5,399,666 A | 3/1995 | Ford | | 5,607,442 A | 3/1997 | Fischell et al. |
| 5,405,472 A | 4/1995 | Leone | | 5,607,467 A | 3/1997 | Froix |
| 5,409,495 A | 4/1995 | Osborn | | 5,609,629 A | 3/1997 | Fearnot et al. |
| 5,411,466 A | 5/1995 | Hess | | 5,610,241 A | 3/1997 | Lee et al. |
| 5,411,477 A | 5/1995 | Saab | | 5,611,775 A | 3/1997 | Machold et al. |
| 5,412,035 A | 5/1995 | Schmitt et al. | | 5,616,338 A | 4/1997 | Fox, Jr. et al. |
| 5,415,938 A | 5/1995 | Cahalan et al. | | 5,618,298 A | 4/1997 | Simon |
| 5,417,981 A | 5/1995 | Endo et al. | | 5,618,299 A | 4/1997 | Khosravi et al. |
| 5,423,849 A | 6/1995 | Engelson et al. | | 5,620,420 A | 4/1997 | Kriesel |
| 5,423,885 A | 6/1995 | Williams | | 5,624,411 A | 4/1997 | Tuch |
| 5,429,618 A | 7/1995 | Keogh | | 5,628,730 A | 5/1997 | Shapland et al. |
| 5,441,515 A | 8/1995 | Khosravi et al. | | 5,628,755 A | 5/1997 | Heller et al. |
| 5,443,458 A | 8/1995 | Eury et al. | | 5,628,781 A | 5/1997 | Williams et al. |
| 5,443,496 A | 8/1995 | Schwartz et al. | | 5,628,785 A | 5/1997 | Schwartz et al. |
| 5,443,500 A | 8/1995 | Sigwart | | 5,628,786 A | 5/1997 | Banas et al. |
| 5,445,646 A | 8/1995 | Euteneuer et al. | | 5,629,077 A | 5/1997 | Turnlund et al. |
| 5,447,724 A | 9/1995 | Helmus et al. | | 5,631,135 A | 5/1997 | Gryaznov et al. |
| 5,451,233 A | 9/1995 | Yock | | 5,632,771 A | 5/1997 | Boatman et al. |
| 5,455,040 A * | 10/1995 | Marchant .................... 424/426 | | 5,632,840 A | 5/1997 | Campbell |
| 5,456,661 A | 10/1995 | Narciso, Jr. | | 5,637,113 A | 6/1997 | Tartaglia et al. |
| 5,456,713 A | 10/1995 | Chuter | | 5,644,020 A | 7/1997 | Timmermann et al. |
| 5,458,615 A | 10/1995 | Klemm et al. | | 5,645,559 A | 7/1997 | Hachtman et al. |
| 5,460,610 A | 10/1995 | Don Michael | | 5,649,951 A | 7/1997 | Davidson |
| 5,462,990 A | 10/1995 | Hubbell et al. | | 5,649,977 A | 7/1997 | Campbell |
| 5,464,450 A | 11/1995 | Buscemi et al. | | 5,653,691 A | 8/1997 | Rupp et al. |
| 5,464,650 A | 11/1995 | Berg et al. | | 5,656,080 A | 8/1997 | Staniforth et al. |
| 5,470,313 A | 11/1995 | Crocker et al. | | 5,656,082 A | 8/1997 | Takatsuki et al. |
| 5,470,603 A | 11/1995 | Staniforth et al. | | 5,658,995 A | 8/1997 | Kohn et al. |
| 5,476,476 A | 12/1995 | Hillstead | | 5,667,523 A | 9/1997 | Bynon et al. |
| 5,476,509 A | 12/1995 | Keogh et al. | | 5,667,767 A | 9/1997 | Greff et al. |
| 5,485,496 A | 1/1996 | Lee et al. | | 5,667,796 A | 9/1997 | Otten |
| 5,496,346 A | 3/1996 | Horzewski et al. | | 5,670,558 A | 9/1997 | Onishi et al. |
| 5,500,013 A | 3/1996 | Buscemi et al. | | 5,674,242 A | 10/1997 | Phan et al. |
| 5,501,227 A | 3/1996 | Yock | | 5,679,400 A | 10/1997 | Tuch |
| 5,502,158 A | 3/1996 | Sinclair et al. | | 5,693,085 A | 12/1997 | Buirge et al. |
| 5,507,768 A | 4/1996 | Lau et al. | | 5,693,376 A | 12/1997 | Fetherston et al. |
| 5,511,726 A | 4/1996 | Greenspan et al. | | 5,695,498 A | 12/1997 | Tower |
| 5,514,154 A | 5/1996 | Lau et al. | | 5,695,810 A | 12/1997 | Dubin et al. |
| 5,514,379 A | 5/1996 | Weissleder et al. | | 5,697,967 A | 12/1997 | Dinh et al. |
| 5,516,560 A | 5/1996 | Harayama et al. | | 5,700,286 A | 12/1997 | Tartaglia et al. |
| 5,516,881 A | 5/1996 | Lee et al. | | 5,702,754 A | 12/1997 | Zhong |
| 5,527,337 A | 6/1996 | Stack et al. | | 5,702,818 A | 12/1997 | Cahalan et al. |
| 5,537,729 A | 7/1996 | Kolobow | | 5,707,385 A | 1/1998 | Williams |
| 5,538,493 A | 7/1996 | Gerken et al. | | 5,711,763 A | 1/1998 | Nonami et al. |

| | | | | | | |
|---|---|---|---|---|---|---|
| 5,711,812 A | 1/1998 | Chapek et al. | | 5,843,119 A | 12/1998 | Schulewitz |
| 5,711,958 A | 1/1998 | Cohn et al. | | 5,843,172 A | 12/1998 | Yan |
| 5,713,949 A | 2/1998 | Jayaraman | | 5,846,247 A | 12/1998 | Unsworth et al. |
| 5,716,981 A | 2/1998 | Hunter et al. | | 5,849,859 A | 12/1998 | Acemoglu |
| 5,718,726 A | 2/1998 | Amon et al. | | 5,851,508 A | 12/1998 | Greff et al. |
| 5,720,726 A | 2/1998 | Marcadis et al. | | 5,853,408 A | 12/1998 | Muni |
| 5,721,131 A | 2/1998 | Rudolph et al. | | 5,854,207 A | 12/1998 | Lee et al. |
| 5,722,984 A | 3/1998 | Fischell et al. | | 5,854,376 A | 12/1998 | Higashi |
| 5,723,219 A | 3/1998 | Kolluri et al. | | 5,855,598 A | 1/1999 | Pinchuk |
| 5,725,549 A | 3/1998 | Lam | | 5,855,612 A | 1/1999 | Ohthuki et al. |
| 5,726,297 A | 3/1998 | Gryaznov et al. | | 5,855,618 A | 1/1999 | Patnaik et al. |
| 5,728,068 A | 3/1998 | Leone et al. | | 5,857,998 A | 1/1999 | Barry |
| 5,728,751 A | 3/1998 | Patnaik | | 5,858,556 A | 1/1999 | Eckhart et al. |
| 5,730,698 A | 3/1998 | Fischell et al. | | 5,858,746 A | 1/1999 | Hubbell et al. |
| 5,733,326 A | 3/1998 | Tomonto et al. | | 5,858,990 A | 1/1999 | Walsh |
| 5,733,327 A | 3/1998 | Igaki et al. | | 5,860,954 A | 1/1999 | Ropiak |
| 5,733,330 A | 3/1998 | Cox | | 5,865,814 A | 2/1999 | Tuch |
| 5,733,564 A | 3/1998 | Lehtinen | | 5,866,113 A | 2/1999 | Hendriks et al. |
| 5,733,925 A | 3/1998 | Kunz et al. | | 5,868,781 A | 2/1999 | Killion |
| 5,735,897 A | 4/1998 | Buirge | | 5,869,127 A | 2/1999 | Zhong |
| 5,741,554 A | 4/1998 | Tisone | | 5,871,436 A | 2/1999 | Eury |
| 5,741,881 A | 4/1998 | Patnaik | | 5,871,437 A | 2/1999 | Alt |
| 5,746,745 A | 5/1998 | Abele et al. | | 5,873,904 A | 2/1999 | Ragheb et al. |
| 5,746,998 A | 5/1998 | Torchilin et al. | | 5,874,101 A | 2/1999 | Zhong et al. |
| 5,756,457 A | 5/1998 | Wang et al. | | 5,874,109 A | 2/1999 | Ducheyne et al. |
| 5,756,476 A | 5/1998 | Epstein et al. | | 5,874,165 A | 2/1999 | Drumheller |
| 5,759,205 A | 6/1998 | Valentini | | 5,874,355 A | 2/1999 | Huang et al. |
| 5,759,474 A | 6/1998 | Rupp et al. | | 5,876,426 A | 3/1999 | Kume et al. |
| 5,765,682 A | 6/1998 | Bley et al. | | 5,876,433 A | 3/1999 | Lunn |
| 5,766,204 A | 6/1998 | Porter et al. | | 5,876,743 A | 3/1999 | Ibsen et al. |
| 5,766,239 A | 6/1998 | Cox | | 5,877,224 A | 3/1999 | Brocchini et al. |
| 5,766,710 A | 6/1998 | Turnlund et al. | | 5,877,263 A | 3/1999 | Patnaik et al. |
| 5,769,883 A | 6/1998 | Buscemi et al. | | 5,879,713 A | 3/1999 | Roth et al. |
| 5,769,884 A | 6/1998 | Solovay | | 5,883,011 A | 3/1999 | Lin et al. |
| 5,770,609 A | 6/1998 | Grainger et al. | | 5,888,533 A | 3/1999 | Dunn |
| 5,772,864 A | 6/1998 | Møller et al. | | 5,891,192 A | 4/1999 | Murayama et al. |
| 5,776,184 A | 7/1998 | Tuch | | 5,893,840 A | 4/1999 | Hull et al. |
| 5,780,807 A | 7/1998 | Saunders | | 5,893,852 A | 4/1999 | Morales |
| 5,782,742 A | 7/1998 | Crocker et al. | | 5,895,407 A | 4/1999 | Jayaraman |
| 5,783,657 A | 7/1998 | Pavlin et al. | | 5,897,911 A | 4/1999 | Loeffler |
| 5,788,626 A | 8/1998 | Thompson | | 5,897,955 A | 4/1999 | Drumheller |
| 5,788,979 A | 8/1998 | Alt et al. | | 5,898,178 A | 4/1999 | Bunker |
| 5,800,392 A | 9/1998 | Racchini | | 5,902,631 A | 5/1999 | Wang et al. |
| 5,800,516 A | 9/1998 | Fine et al. | | 5,902,875 A | 5/1999 | Roby et al. |
| 5,804,318 A * | 9/1998 | Pinchuk et al. ............. 428/421 | | 5,905,168 A | 5/1999 | Dos Santos et al. |
| 5,807,244 A | 9/1998 | Barot | | 5,906,759 A | 5/1999 | Richter |
| 5,810,871 A | 9/1998 | Tuckey et al. | | 5,910,564 A | 6/1999 | Gruning et al. |
| 5,810,873 A | 9/1998 | Morales | | 5,914,182 A | 6/1999 | Drumheller |
| 5,811,151 A | 9/1998 | Hendriks et al. | | 5,914,387 A | 6/1999 | Roby et al. |
| 5,811,447 A | 9/1998 | Kunz et al. | | 5,916,234 A | 6/1999 | Lam |
| 5,820,917 A | 10/1998 | Tuch | | 5,916,870 A | 6/1999 | Lee et al. |
| 5,823,996 A | 10/1998 | Sparks | | 5,919,893 A | 7/1999 | Roby et al. |
| 5,824,048 A | 10/1998 | Tuch | | 5,921,416 A | 7/1999 | Uchara |
| 5,824,049 A | 10/1998 | Ragheb et al. | | 5,922,005 A | 7/1999 | Richter et al. |
| 5,824,056 A | 10/1998 | Rosenberg | | 5,922,393 A | 7/1999 | Jayaraman |
| 5,826,586 A | 10/1998 | Mishra et al. | | 5,925,552 A | 7/1999 | Keogh et al. |
| 5,830,178 A | 11/1998 | Jones et al. | | 5,925,720 A | 7/1999 | Kataoka et al. |
| 5,830,179 A | 11/1998 | Mikus et al. | | 5,928,916 A | 7/1999 | Keogh |
| 5,830,217 A | 11/1998 | Ryan | | 5,932,299 A | 8/1999 | Katoot |
| 5,830,461 A | 11/1998 | Billiar | | 5,935,135 A | 8/1999 | Bramfitt et al. |
| 5,830,879 A | 11/1998 | Isner | | 5,942,209 A | 8/1999 | Leavitt et al. |
| 5,833,644 A | 11/1998 | Zadno-Azizi et al. | | 5,947,993 A | 9/1999 | Morales |
| 5,833,651 A | 11/1998 | Donovan et al. | | 5,948,018 A | 9/1999 | Dereume et al. |
| 5,833,659 A | 11/1998 | Kranys | | 5,948,428 A | 9/1999 | Lee et al. |
| 5,834,582 A | 11/1998 | Sinclair et al. | | 5,951,881 A | 9/1999 | Rogers et al. |
| 5,836,962 A | 11/1998 | Gianotti | | 5,954,744 A | 9/1999 | Phan et al. |
| 5,836,965 A | 11/1998 | Jendersee et al. | | 5,955,509 A | 9/1999 | Webber et al. |
| 5,837,008 A | 11/1998 | Berg et al. | | 5,957,975 A | 9/1999 | Lafont et al. |
| 5,837,313 A | 11/1998 | Ding et al. | | 5,958,385 A | 9/1999 | Tondeur et al. |
| 5,837,835 A | 11/1998 | Gryaznov et al. | | 5,962,138 A | 10/1999 | Kolluri et al. |
| 5,840,009 A | 11/1998 | Fischell et al. | | 5,965,720 A | 10/1999 | Gryaznov et al. |
| 5,840,083 A | 11/1998 | Braach-Maksvytis | | 5,968,091 A | 10/1999 | Pinchuk et al. |
| 5,843,033 A | 12/1998 | Ropiak | | 5,968,092 A | 10/1999 | Buscemi et al. |

| Patent No. | Date | Inventor |
|---|---|---|
| 5,969,422 A | 10/1999 | Ting et al. |
| 5,971,954 A | 10/1999 | Conway et al. |
| 5,972,027 A | 10/1999 | Johnson |
| 5,972,029 A | 10/1999 | Fuisz |
| 5,972,505 A | 10/1999 | Phillips et al. |
| 5,976,155 A | 11/1999 | Foreman et al. |
| 5,976,182 A | 11/1999 | Cox |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,984,449 A | 11/1999 | Tajika et al. |
| 5,986,169 A | 11/1999 | Gjunter |
| 5,997,468 A | 12/1999 | Wolff et al. |
| 5,997,517 A * | 12/1999 | Whitbourne ............... 604/265 |
| 6,010,445 A | 1/2000 | Armini et al. |
| 6,010,530 A | 1/2000 | Goicoechea |
| 6,010,573 A | 1/2000 | Bowlin |
| 6,011,125 A | 1/2000 | Lohmeijer et al. |
| 6,013,099 A | 1/2000 | Dinh et al. |
| 6,015,541 A | 1/2000 | Greff et al. |
| 6,019,789 A | 2/2000 | Dinh et al. |
| 6,024,918 A | 2/2000 | Hendriks et al. |
| 6,027,510 A | 2/2000 | Alt |
| 6,027,526 A | 2/2000 | Limon et al. |
| 6,030,371 A | 2/2000 | Pursley |
| 6,033,582 A | 3/2000 | Lee et al. |
| 6,033,719 A | 3/2000 | Keogh |
| 6,034,204 A | 3/2000 | Mohr et al. |
| 6,042,606 A | 3/2000 | Frantzen |
| 6,042,875 A | 3/2000 | Ding et al. |
| 6,045,899 A | 4/2000 | Wang et al. |
| 6,048,964 A | 4/2000 | Lee et al. |
| 6,051,021 A | 4/2000 | Frid |
| 6,051,576 A | 4/2000 | Ashton et al. |
| 6,051,648 A | 4/2000 | Rhee et al. |
| 6,054,553 A | 4/2000 | Groth et al. |
| 6,056,906 A | 5/2000 | Werneth et al. |
| 6,056,993 A | 5/2000 | Leidner et al. |
| 6,059,752 A | 5/2000 | Segal |
| 6,059,810 A | 5/2000 | Brown et al. |
| 6,060,451 A | 5/2000 | DiMaio et al. |
| 6,060,518 A | 5/2000 | Kabanov et al. |
| 6,063,092 A | 5/2000 | Shin |
| 6,066,156 A | 5/2000 | Yan |
| 6,071,266 A | 6/2000 | Kelley |
| 6,071,305 A | 6/2000 | Brown et al. |
| 6,074,659 A | 6/2000 | Kunz et al. |
| 6,080,099 A | 6/2000 | Slater et al. |
| 6,080,177 A | 6/2000 | Igaki et al. |
| 6,080,190 A | 6/2000 | Schwartz |
| 6,080,488 A | 6/2000 | Hostettler et al. |
| 6,083,258 A | 7/2000 | Yadav |
| 6,086,610 A | 7/2000 | Duerig et al. |
| 6,090,330 A | 7/2000 | Gawa et al. |
| 6,093,199 A | 7/2000 | Brown et al. |
| 6,093,463 A | 7/2000 | Thakrar |
| 6,096,070 A | 8/2000 | Ragheb et al. |
| 6,096,525 A | 8/2000 | Patnaik |
| 6,099,455 A | 8/2000 | Columbo et al. |
| 6,099,559 A | 8/2000 | Nolting |
| 6,099,561 A | 8/2000 | Alt |
| 6,099,562 A | 8/2000 | Ding et al. |
| 6,103,230 A | 8/2000 | Billiar et al. |
| 6,106,454 A | 8/2000 | Berg et al. |
| 6,106,530 A | 8/2000 | Harada |
| 6,106,889 A | 8/2000 | Beavers et al. |
| 6,107,416 A | 8/2000 | Patnaik et al. |
| 6,110,180 A | 8/2000 | Foreman et al. |
| 6,110,188 A | 8/2000 | Narciso, Jr. |
| 6,110,483 A | 8/2000 | Whitbourne et al. |
| 6,113,629 A | 9/2000 | Ken |
| 6,117,479 A | 9/2000 | Hogan et al. |
| 6,117,979 A | 9/2000 | Hendriks et al. |
| 6,120,477 A | 9/2000 | Campbell et al. |
| 6,120,491 A | 9/2000 | Kohn et al. |
| 6,120,535 A | 9/2000 | McDonald et al. |
| 6,120,536 A | 9/2000 | Ding et al. |
| 6,120,788 A | 9/2000 | Barrows |
| 6,120,847 A | 9/2000 | Yang et al. |
| 6,120,904 A | 9/2000 | Hostettler et al. |
| 6,121,027 A | 9/2000 | Clapper et al. |
| 6,123,712 A | 9/2000 | Di Caprio et al. |
| 6,125,523 A | 10/2000 | Brown et al. |
| 6,126,686 A | 10/2000 | Badylak et al. |
| 6,127,173 A | 10/2000 | Eckstein et al. |
| 6,129,761 A | 10/2000 | Hubbell |
| 6,129,928 A | 10/2000 | Sarangapani et al. |
| 6,132,809 A | 10/2000 | Hynes et al. |
| 6,136,333 A | 10/2000 | Cohn et al. |
| 6,140,127 A | 10/2000 | Sprague |
| 6,140,431 A | 10/2000 | Kinker et al. |
| 6,143,354 A | 11/2000 | Koulik et al. |
| 6,143,370 A | 11/2000 | Panagiotou et al. |
| 6,149,574 A | 11/2000 | Trauthen et al. |
| 6,150,630 A | 11/2000 | Perry et al. |
| 6,153,252 A | 11/2000 | Hossainy et al. |
| 6,156,373 A | 12/2000 | Zhong et al. |
| 6,159,227 A | 12/2000 | Di Caprio et al. |
| 6,159,229 A | 12/2000 | Jendersee et al. |
| 6,159,951 A | 12/2000 | Karpeisky et al. |
| 6,159,978 A | 12/2000 | Myers et al. |
| 6,160,084 A | 12/2000 | Langer et al. |
| 6,165,212 A | 12/2000 | Dereume et al. |
| 6,166,130 A | 12/2000 | Rhee et al. |
| 6,168,617 B1 | 1/2001 | Blaeser et al. |
| 6,168,619 B1 | 1/2001 | Dinh et al. |
| 6,169,170 B1 | 1/2001 | Gryaznov et al. |
| 6,171,609 B1 | 1/2001 | Kunz |
| 6,172,167 B1 | 1/2001 | Stapert et al. |
| 6,174,316 B1 | 1/2001 | Tuckey et al. |
| 6,174,330 B1 | 1/2001 | Stinson |
| 6,177,523 B1 | 1/2001 | Reich et al. |
| 6,180,632 B1 | 1/2001 | Myers et al. |
| 6,183,505 B1 | 2/2001 | Mohn, Jr. et al. |
| 6,187,045 B1 | 2/2001 | Fehring et al. |
| 6,193,727 B1 | 2/2001 | Foreman et al. |
| 6,203,551 B1 | 3/2001 | Wu |
| 6,209,621 B1 | 4/2001 | Treacy |
| 6,210,715 B1 | 4/2001 | Starling et al. |
| 6,211,249 B1 | 4/2001 | Cohn et al. |
| 6,214,115 B1 | 4/2001 | Taylor et al. |
| 6,214,407 B1 | 4/2001 | Laube et al. |
| 6,214,901 B1 | 4/2001 | Chudzik et al. |
| 6,217,586 B1 | 4/2001 | Mackenzie |
| 6,217,721 B1 | 4/2001 | Xu et al. |
| 6,224,626 B1 | 5/2001 | Steinke |
| 6,224,675 B1 | 5/2001 | Prentice et al. |
| 6,224,894 B1 | 5/2001 | Jamiolkowski et al. |
| 6,228,845 B1 | 5/2001 | Donovan et al. |
| 6,231,590 B1 | 5/2001 | Slaikeu et al. |
| 6,231,600 B1 | 5/2001 | Zhong |
| 6,240,616 B1 | 6/2001 | Yan |
| 6,242,041 B1 | 6/2001 | Katoot et al. |
| 6,245,076 B1 | 6/2001 | Yan |
| 6,245,099 B1 | 6/2001 | Edwin et al. |
| 6,245,103 B1 | 6/2001 | Stinson |
| 6,245,753 B1 | 6/2001 | Byun et al. |
| 6,245,760 B1 | 6/2001 | He et al. |
| 6,248,129 B1 | 6/2001 | Froix |
| 6,248,344 B1 | 6/2001 | Ylanen et al. |
| 6,251,135 B1 | 6/2001 | Stinson et al. |
| 6,251,136 B1 | 6/2001 | Guruwaiya et al. |
| 6,251,142 B1 | 6/2001 | Bernacca et al. |
| 6,253,443 B1 | 7/2001 | Johnson |
| 6,254,632 B1 | 7/2001 | Wu et al. |

| | | | | | |
|---|---|---|---|---|---|
| 6,258,099 B1 | 7/2001 | Mareiro et al. | 6,495,200 B1 | 12/2002 | Chan et al. |
| 6,258,121 B1 | 7/2001 | Yang et al. | 6,503,538 B1 | 1/2003 | Chu et al. |
| 6,258,371 B1 | 7/2001 | Koulik et al. | 6,503,556 B1 | 1/2003 | Harish et al. |
| 6,262,034 B1 | 7/2001 | Mathiowitz et al. | 6,503,954 B1 | 1/2003 | Bhat et al. |
| 6,270,788 B1 | 8/2001 | Koulik et al. | 6,504,307 B1 | 1/2003 | Malik et al. |
| 6,273,850 B1 | 8/2001 | Gambale | 6,506,437 B1 | 1/2003 | Harish et al. |
| 6,273,913 B1 | 8/2001 | Wright et al. | 6,510,722 B1 | 1/2003 | Ching et al. |
| 6,277,110 B1 | 8/2001 | Morales | 6,511,748 B1 | 1/2003 | Barrows |
| 6,277,449 B1 | 8/2001 | Kolluri et al. | 6,517,888 B1 | 2/2003 | Weber |
| 6,279,368 B1 | 8/2001 | Escano et al. | 6,517,889 B1 | 2/2003 | Jayaraman |
| 6,281,262 B1 | 8/2001 | Shikinami | 6,521,284 B1 | 2/2003 | Parsons et al. |
| 6,283,947 B1 | 9/2001 | Mirzaee | 6,524,232 B1 | 2/2003 | Tang et al. |
| 6,283,949 B1 | 9/2001 | Roorda | 6,524,347 B1 | 2/2003 | Myers et al. |
| 6,284,305 B1 | 9/2001 | Ding et al. | 6,527,801 B1 | 3/2003 | Dutta |
| 6,284,333 B1 | 9/2001 | Wang et al. | 6,527,863 B1 | 3/2003 | Pacetti et al. |
| 6,287,332 B1 | 9/2001 | Bolz et al. | 6,528,526 B1 | 3/2003 | Myers et al. |
| 6,287,628 B1 | 9/2001 | Hossainy et al. | 6,530,950 B1 | 3/2003 | Alvarado et al. |
| 6,290,721 B1 | 9/2001 | Heath | 6,530,951 B1 | 3/2003 | Bates et al. |
| 6,293,966 B1 | 9/2001 | Frantzen | 6,537,589 B1 | 3/2003 | Chae et al. |
| 6,294,836 B1 | 9/2001 | Paranjpe et al. | 6,539,607 B1 | 4/2003 | Fehring et al. |
| 6,296,603 B1 | 10/2001 | Turnlund et al. | 6,540,776 B1 | 4/2003 | Sanders Millare et al. |
| 6,299,604 B1 | 10/2001 | Ragheb et al. | 6,540,777 B1 | 4/2003 | Stenzel |
| 6,303,901 B1 | 10/2001 | Perry et al. | 6,544,223 B1 | 4/2003 | Kokish |
| 6,306,176 B1 | 10/2001 | Whitbourne | 6,544,543 B1 | 4/2003 | Mandrusov et al. |
| 6,312,459 B1 | 11/2001 | Huang et al. | 6,544,582 B1 | 4/2003 | Yoe |
| 6,319,520 B1 | 11/2001 | Wuthrich et al. | 6,554,758 B1 | 4/2003 | Turnlund et al. |
| 6,322,588 B1 | 11/2001 | Ogle et al. | 6,554,854 B1 | 4/2003 | Flanagan |
| 6,322,847 B1 | 11/2001 | Zhong et al. | 6,555,059 B1 | 4/2003 | Myrick et al. |
| 6,327,772 B1 | 12/2001 | Zadno-Azizi et al. | 6,555,157 B1 | 4/2003 | Hossainy |
| 6,331,313 B1 | 12/2001 | Wong et al. | 6,558,733 B1 | 5/2003 | Hossainy et al. |
| 6,335,029 B1 | 1/2002 | Kamath et al. | 6,562,136 B1 | 5/2003 | Chappa et al. |
| 6,344,035 B1 | 2/2002 | Chudzik et al. | 6,565,599 B1 | 5/2003 | Hong et al. |
| 6,346,110 B1 | 2/2002 | Wu | 6,565,659 B1 | 5/2003 | Pacetti et al. |
| 6,358,556 B1 | 3/2002 | Ding et al. | 6,569,191 B1 | 5/2003 | Hogan |
| 6,362,099 B1 | 3/2002 | Gandikota et al. | 6,569,193 B1 | 5/2003 | Cox et al. |
| 6,364,903 B1 | 4/2002 | Tseng et al. | 6,572,644 B1 | 6/2003 | Moein |
| 6,375,458 B1 | 4/2002 | Moorleghem et al. | 6,572,672 B1 | 6/2003 | Yadav et al. |
| 6,375,826 B1 | 4/2002 | Wang et al. | 6,574,851 B1 | 6/2003 | Mirizzi |
| 6,379,379 B1 | 4/2002 | Wang | 6,582,417 B1 | 6/2003 | Ledesma et al. |
| 6,379,381 B1 | 4/2002 | Hossainy et al. | 6,585,755 B1 | 7/2003 | Jackson et al. |
| 6,387,118 B1 | 5/2002 | Hanson | 6,585,765 B1 | 7/2003 | Hossainy et al. |
| 6,387,121 B1 | 5/2002 | Alt | 6,585,926 B1 | 7/2003 | Mirzaee |
| 6,387,379 B1 | 5/2002 | Goldberg et al. | 6,592,614 B1 | 7/2003 | Lenker et al. |
| 6,388,043 B1 | 5/2002 | Langer et al. | 6,592,617 B1 | 7/2003 | Thompson |
| 6,395,325 B1 | 5/2002 | Hedge et al. | 6,596,296 B1 | 7/2003 | Nelson et al. |
| 6,395,326 B1 | 5/2002 | Castro et al. | 6,605,114 B1 * | 8/2003 | Yan et al. .................. 623/1.43 |
| 6,406,738 B1 | 6/2002 | Hogan et al. | 6,605,154 B1 | 8/2003 | Villareal |
| 6,409,761 B1 | 6/2002 | Jang | 6,605,874 B1 | 8/2003 | Leu et al. |
| 6,413,272 B1 | 7/2002 | Igaki | 6,610,087 B1 | 8/2003 | Zarbatany et al. |
| 6,419,692 B1 | 7/2002 | Yang et al. | 6,613,072 B1 | 9/2003 | Lau et al. |
| 6,420,189 B1 | 7/2002 | Lopatin | 6,616,765 B1 | 9/2003 | Castro et al. |
| 6,423,092 B1 | 7/2002 | Datta et al. | 6,623,448 B1 | 9/2003 | Slater |
| 6,436,816 B1 | 8/2002 | Lee et al. | 6,625,486 B1 | 9/2003 | Lundkvist et al. |
| 6,444,567 B1 | 9/2002 | Besser et al. | 6,626,939 B1 | 9/2003 | Burnside et al. |
| 6,447,835 B1 | 9/2002 | Wang et al. | 6,635,269 B1 | 10/2003 | Jennissen |
| 6,451,373 B1 | 9/2002 | Hossainy et al. | 6,635,964 B1 | 10/2003 | Maex et al. |
| 6,454,738 B1 | 9/2002 | Tran et al. | 6,645,135 B1 | 11/2003 | Bhat |
| 6,455,424 B1 | 9/2002 | McTeer et al. | 6,645,195 B1 | 11/2003 | Bhat et al. |
| 6,461,632 B1 | 10/2002 | Gogolewski | 6,645,243 B1 | 11/2003 | Vallana et al. |
| 6,462,284 B1 | 10/2002 | Hashimoto | 6,645,547 B1 | 11/2003 | Shekalim et al. |
| 6,464,720 B1 | 10/2002 | Boatman et al. | 6,656,162 B1 | 12/2003 | Santini, Jr. et al. |
| 6,468,906 B1 | 10/2002 | Chan et al. | 6,656,216 B1 | 12/2003 | Hossainy et al. |
| 6,479,565 B1 | 11/2002 | Stanley | 6,656,506 B1 | 12/2003 | Wu et al. |
| 6,481,262 B1 | 11/2002 | Ching et al. | 6,660,034 B1 | 12/2003 | Mandrusov et al. |
| 6,482,834 B1 | 11/2002 | Spada et al. | 6,663,662 B1 | 12/2003 | Pacetti et al. |
| 6,485,512 B1 | 11/2002 | Cheng | 6,663,880 B1 | 12/2003 | Roorda et al. |
| 6,488,701 B1 | 12/2002 | Nolting et al. | 6,664,187 B1 | 12/2003 | Ngo et al. |
| 6,488,773 B1 | 12/2002 | Ehrhardt et al. | 6,664,335 B1 | 12/2003 | Krishnan |
| 6,491,666 B1 | 12/2002 | Santini, Jr. et al. | 6,666,214 B1 | 12/2003 | Canham |
| 6,492,615 B1 | 12/2002 | Flanagan | 6,666,880 B1 | 12/2003 | Chiu et al. |
| 6,494,862 B1 | 12/2002 | Ray et al. | 6,667,049 B1 | 12/2003 | Janas et al. |
| 6,494,908 B1 | 12/2002 | Huxel et al. | 6,669,723 B1 | 12/2003 | Killion et al. |
| 6,495,156 B1 | 12/2002 | Wenz et al. | 6,669,980 B1 | 12/2003 | Hansen |

| Patent/Pub No. | Date | Inventor |
|---|---|---|
| 6,673,154 B1 | 1/2004 | Pacetti et al. |
| 6,673,385 B1 | 1/2004 | Ding et al. |
| 6,676,697 B1 | 1/2004 | Richter |
| 6,676,700 B1 | 1/2004 | Jacobs et al. |
| 6,679,980 B1 | 1/2004 | Andreacchi |
| 6,689,099 B1 | 2/2004 | Mirzaee |
| 6,689,375 B1 | 2/2004 | Wahlig et al. |
| 6,695,920 B1 | 2/2004 | Pacetti et al. |
| 6,703,307 B1 | 3/2004 | Lopatin et al. |
| 6,706,013 B1 | 3/2004 | Bhat et al. |
| 6,706,273 B1 | 3/2004 | Roessler |
| 6,709,379 B1 | 3/2004 | Brandau et al. |
| 6,709,514 B1 | 3/2004 | Hossainy |
| 6,712,845 B1 | 3/2004 | Hossainy |
| 6,713,119 B1 | 3/2004 | Hossainy et al. |
| 6,716,444 B1 | 4/2004 | Castro et al. |
| 6,719,934 B1 | 4/2004 | Stinson |
| 6,719,989 B1 | 4/2004 | Matsushima et al. |
| 6,720,402 B1 | 4/2004 | Langer et al. |
| 6,723,120 B1 | 4/2004 | Yan |
| 6,733,768 B1 | 5/2004 | Hossainy et al. |
| 6,740,040 B1 | 5/2004 | Mandrusov et al. |
| 6,743,462 B1 | 6/2004 | Pacetti |
| 6,746,773 B1 | 6/2004 | Llanos et al. |
| 6,749,626 B1 | 6/2004 | Bhat et al. |
| 6,752,826 B1 | 6/2004 | Holloway et al. |
| 6,753,007 B1 | 6/2004 | Haggard et al. |
| 6,753,071 B1 | 6/2004 | Pacetti et al. |
| 6,758,859 B1 | 7/2004 | Dang et al. |
| 6,759,054 B1 | 7/2004 | Chen et al. |
| 6,764,505 B1 | 7/2004 | Hossainy et al. |
| 6,774,278 B1 | 8/2004 | Ragheb et al. |
| 6,776,792 B1 * | 8/2004 | Yan et al. ............... 623/1.15 |
| 6,783,793 B1 | 8/2004 | Hossainy et al. |
| 6,818,063 B1 | 11/2004 | Kerrigan |
| 6,846,323 B1 | 1/2005 | Yip et al. |
| 6,860,946 B1 | 3/2005 | Hossainy et al. |
| 6,861,088 B1 | 3/2005 | Weber et al. |
| 6,865,810 B1 | 3/2005 | Stinson |
| 6,869,443 B1 | 3/2005 | Buscemi et al. |
| 6,878,160 B1 | 4/2005 | Gilligan et al. |
| 6,887,270 B1 | 5/2005 | Miller et al. |
| 6,887,485 B1 | 5/2005 | Fitzhugh et al. |
| 6,890,546 B1 | 5/2005 | Mollison et al. |
| 6,899,731 B1 | 5/2005 | Li et al. |
| 2001/0007083 A1 | 7/2001 | Roorda |
| 2001/0014717 A1 | 8/2001 | Hossainy et al. |
| 2001/0016753 A1 | 8/2001 | Caprio et al. |
| 2001/0020011 A1 | 9/2001 | Mathiowitz et al. |
| 2001/0029351 A1 | 10/2001 | Falotico et al. |
| 2001/0037145 A1 | 11/2001 | Guruwaiya et al. |
| 2001/0044652 A1 | 11/2001 | Moore |
| 2001/0051608 A1 | 12/2001 | Mathiowitz et al. |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0062148 A1 | 5/2002 | Hart |
| 2002/0065553 A1 | 5/2002 | Weber |
| 2002/0071822 A1 | 6/2002 | Uhrich |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0091433 A1 | 7/2002 | Ding et al. |
| 2002/0094440 A1 | 7/2002 | Llanos et al. |
| 2002/0111590 A1 | 8/2002 | Davila et al. |
| 2002/0116050 A1 | 8/2002 | Kocur |
| 2002/0120326 A1 | 8/2002 | Michal |
| 2002/0138133 A1 | 9/2002 | Lenz et al. |
| 2002/0142039 A1 | 10/2002 | Claude |
| 2002/0155212 A1 | 10/2002 | Hossainy |
| 2002/0161114 A1 | 10/2002 | Gunatillake et al. |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0187632 A1 | 12/2002 | Marsh |
| 2002/0188037 A1 | 12/2002 | Chudzik et al. |
| 2002/0188277 A1 | 12/2002 | Roorda et al. |
| 2003/0003221 A1 | 1/2003 | Zhong et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0033001 A1 | 2/2003 | Igaki |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0054090 A1 | 3/2003 | Hansen |
| 2003/0055482 A1 | 3/2003 | Schwager et al. |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0088307 A1 | 5/2003 | Shulze et al. |
| 2003/0093107 A1 | 5/2003 | Parsonage et al. |
| 2003/0097088 A1 | 5/2003 | Pacetti |
| 2003/0097173 A1 | 5/2003 | Dutta |
| 2003/0099712 A1 | 5/2003 | Jayaraman |
| 2003/0100865 A1 | 5/2003 | Santini, Jr. et al. |
| 2003/0105518 A1 | 6/2003 | Dutta |
| 2003/0105530 A1 | 6/2003 | Pirhonen |
| 2003/0113439 A1 | 6/2003 | Pacetti et al. |
| 2003/0113445 A1 | 6/2003 | Martin |
| 2003/0138487 A1 | 7/2003 | Hogan et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0171053 A1 | 9/2003 | Sanders |
| 2003/0185964 A1 | 10/2003 | Weber et al. |
| 2003/0187495 A1 | 10/2003 | Cully et al. |
| 2003/0190406 A1 | 10/2003 | Hossainy et al. |
| 2003/0203617 A1 | 10/2003 | Lane et al. |
| 2003/0207020 A1 | 11/2003 | Villareal |
| 2003/0208259 A1 | 11/2003 | Penhasi |
| 2003/0209835 A1 | 11/2003 | Chun et al. |
| 2003/0211230 A1 | 11/2003 | Pacetti et al. |
| 2003/0226833 A1 | 12/2003 | Shapovalov et al. |
| 2003/0236565 A1 | 12/2003 | DiMatteo et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |

| | | | | | | |
|---|---|---|---|---|---|---|
| 2004/0093077 A1 | 5/2004 | White et al. | | GB | 2 333 975 | 1/2000 |
| 2004/0096504 A1 | 5/2004 | Michal | | GB | 2 336 551 | 1/2000 |
| 2004/0098095 A1 | 5/2004 | Burnside et al. | | GB | 2 356 586 | 5/2001 |
| 2004/0098117 A1 | 5/2004 | Hossainy et al. | | GB | 2 356 587 | 5/2001 |
| 2004/0111149 A1 | 6/2004 | Stinson | | GB | 2 333 474 | 6/2001 |
| | | | | GB | 2 334 685 | 6/2001 |
| | FOREIGN PATENT DOCUMENTS | | | GB | 2 356 585 | 7/2001 |
| | | | | GB | 2 374 302 | 8/2001 |
| CA | 2 007 648 | 4/1991 | | GB | 2 370 243 | 6/2002 |
| CA | 1 322 628 | 10/1993 | | GB | 2 384 199 | 7/2003 |
| CA | 1 336 319 | 7/1995 | | JP | SHO49-48336 | 12/1974 |
| CA | 1 338 303 | 5/1996 | | JP | SHO54-18310 | 7/1979 |
| DE | 042 24 401 | 1/1994 | | JP | SHO60-28504 | 7/1985 |
| DE | 044 07 079 | 9/1994 | | JP | 21199867 | 5/1994 |
| DE | 197 31 021 | 1/1999 | | JP | HEI8-33718 | 2/1996 |
| DE | 199 16 086 | 10/1999 | | JP | HEI10-151190 | 6/1998 |
| DE | 198 56 983 | 12/1999 | | JP | 2919971 B2 | 7/1999 |
| EP | 0 108 171 | 5/1984 | | JP | 2001-190687 | 7/2001 |
| EP | 0 144 534 | 6/1985 | | SU | 0872531 | 10/1981 |
| EP | 0 301 856 | 2/1989 | | SU | 0876663 | 10/1981 |
| EP | 0 380 668 | 4/1989 | | SU | 0905228 | 2/1982 |
| EP | 0 351 314 | 1/1990 | | SU | 0790725 | 2/1983 |
| EP | 0 364 787 | 4/1990 | | SU | 1016314 | 5/1983 |
| EP | 0 396 429 | 11/1990 | | SU | 0811750 | 9/1983 |
| EP | 0 397 500 | 11/1990 | | SU | 1293518 | 2/1987 |
| EP | 0 464 755 | 1/1992 | | SU | 1477423 | 5/1989 |
| EP | 0 493 788 | 7/1992 | | WO | WO 89/03232 | 4/1989 |
| EP | 0 526 606 | 9/1992 | | WO | WO 90/01969 | 3/1990 |
| EP | 0 514 406 | 11/1992 | | WO | WO 90/04982 | 5/1990 |
| EP | 0 517 075 | 12/1992 | | WO | WO 90/06094 | 6/1990 |
| EP | 0 540 290 | 5/1993 | | WO | WO 91/11176 | 8/1991 |
| EP | 0 553 960 | 8/1993 | | WO | WO 91/12846 | 9/1991 |
| EP | 0 554 082 | 8/1993 | | WO | WO 91/17744 | 11/1991 |
| EP | 0 565 251 | 10/1993 | | WO | WO 91/17789 | 11/1991 |
| EP | 0 578 998 | 1/1994 | | WO | WO 92/10218 | 6/1992 |
| EP | 0 604 022 | 6/1994 | | WO | WO 93/06792 | 4/1993 |
| EP | 0 621 017 | 10/1994 | | WO | WO 94/09760 | 5/1994 |
| EP | 0 623 354 | 11/1994 | | WO | WO 94/21196 | 9/1994 |
| EP | 0 627 226 | 12/1994 | | WO | WO 95/10989 | 4/1995 |
| EP | 0 649 637 | 4/1995 | | WO | WO 95/11817 | 5/1995 |
| EP | 0 665 023 | 8/1995 | | WO | WO 95/24929 | 9/1995 |
| EP | 0 701 802 | 3/1996 | | WO | WO 95/29647 | 11/1995 |
| EP | 0 701 803 | 3/1996 | | WO | WO 95/33422 | 12/1995 |
| EP | 0 709 068 | 5/1996 | | WO | WO 96/28115 | 9/1996 |
| EP | 0 716 836 | 6/1996 | | WO | WO 96/35516 | 11/1996 |
| EP | 0 732 087 | 9/1996 | | WO | WO 96/40174 | 12/1996 |
| EP | 0 832 618 | 9/1996 | | WO | WO 97/10011 | 3/1997 |
| EP | 0 756 853 | 2/1997 | | WO | WO 97/45105 | 12/1997 |
| EP | 0 809 999 | 12/1997 | | WO | WO 97/46590 | 12/1997 |
| EP | 0 832 655 | 4/1998 | | WO | WO 98/04415 | 2/1998 |
| EP | 0 834 293 | 4/1998 | | WO | WO 98/07390 | 2/1998 |
| EP | 0 850 604 | 7/1998 | | WO | WO 98/08463 | 3/1998 |
| EP | 0 850 651 | 7/1998 | | WO | WO 98/17331 | 4/1998 |
| EP | 0 879 595 | 11/1998 | | WO | WO 98/20863 | 5/1998 |
| EP | 0 910 584 | 4/1999 | | WO | WO 98/23228 | 6/1998 |
| EP | 0 923 953 | 6/1999 | | WO | WO 98/32398 | 7/1998 |
| EP | 0 953 320 | 11/1999 | | WO | WO 98/36784 | 8/1998 |
| EP | 0 970 711 | 1/2000 | | WO | WO 99/01118 | 1/1999 |
| EP | 0 972 498 | 1/2000 | | WO | WO 99/03515 | 1/1999 |
| EP | 0 974 315 | 1/2000 | | WO | WO 99/16386 | 4/1999 |
| EP | 0 982 041 | 3/2000 | | WO | WO 99/38546 | 8/1999 |
| EP | 1 023 879 | 8/2000 | | WO | WO 99/42147 | 8/1999 |
| EP | 1 034 752 | 9/2000 | | WO | WO 99/63981 | 12/1999 |
| EP | 1 075 838 | 2/2001 | | WO | WO 00/02599 | 1/2000 |
| EP | 1 103 234 | 5/2001 | | WO | WO 00/12147 | 3/2000 |
| EP | 1 192 957 | 4/2002 | | WO | WO 00/18446 | 4/2000 |
| EP | 1 273 314 | 1/2003 | | WO | WO 00/64506 | 11/2000 |
| EP | 0 869 847 | 3/2003 | | WO | WO 01/01890 | 1/2001 |
| EP | 0 941 072 | 1/2004 | | WO | WO 01/15751 | 3/2001 |
| FR | 2 753 907 | 4/1998 | | WO | WO 01/17459 | 3/2001 |
| GB | 2 247 696 | 3/1992 | | WO | WO 01/17577 | 3/2001 |
| GB | 2 316 086 | 1/2000 | | WO | WO 01/43727 | 6/2001 |
| GB | 2 316 342 | 1/2000 | | WO | WO 01/45763 | 6/2001 |

| | | |
|---|---|---|
| WO | WO 01/49338 | 7/2001 |
| WO | WO 01/51027 | 7/2001 |
| WO | WO 01/52772 | 7/2001 |
| WO | WO 01/57144 | 8/2001 |
| WO | WO 01/74414 | 10/2001 |
| WO | WO 01/91918 | 12/2001 |
| WO | WO 02/03890 | 1/2002 |
| WO | WO 02/026162 | 4/2002 |
| WO | WO 02/034311 | 5/2002 |
| WO | WO 02/047731 | 6/2002 |
| WO | WO 02/049771 | 6/2002 |
| WO | WO 02/056790 | 7/2002 |
| WO | WO 02/058753 | 8/2002 |
| WO | WO 02/087550 | 11/2002 |
| WO | WO 02/102283 | 12/2002 |
| WO | WO 03/000308 | 1/2003 |
| WO | WO 03/007918 | 1/2003 |
| WO | WO 03/007919 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/061841 | 7/2003 |
| WO | WO 03/072084 | 9/2003 |
| WO | WO 03/072086 | 9/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |
| WO | WO 2004/017947 | 3/2004 |
| WO | WO 2004/017976 | 3/2004 |
| WO | WO 2004/023985 | 3/2004 |
| WO | WO 2004/024339 | 3/2004 |

OTHER PUBLICATIONS

U.S. Appl. No. 10/304,669, filed Nov. 25, 2002, Madriaga et al.
U.S. Appl. No. 10/317,435, filed Dec. 11, 2002, Hossainy et al.
U.S. Appl. No. 10/322,255, filed Dec. 17, 2002, Chen et al.
U.S. Appl. No. 10/409,410, filed Apr. 7, 2003, Pacetti.
U.S. Appl. No. 10/439,415, filed May 15, 2003, Perng.
U.S. Appl. No. 10/602,487, filed Jun. 23, 2003, Castro et al.
U.S. Appl. No. 10/630,250, filed Jul. 30, 2003, Pacetti et al.
U.S. Appl. No. 10/676,545, filed Sep. 30, 2003, Fox et al.
U.S. Appl. No. 10/680,905, filed Oct. 7, 2003, Pacetti et al.
U.S. Appl. No. 10/738,704, filed Dec. 16, 2003, Pacetti et al.
U.S. Appl. No. 10/741,214, filed Dec. 19, 2003, Pacetti.
U.S. Appl. No. 10/747,996, filed Dec. 29, 2003, Chen et al.
U.S. Appl. No. 10/750,139, filed Dec. 30, 2003, DesNoyer et al.
U.S. Appl. No. 10/805,036, filed Mar. 16, 2004, Pacetti.
U.S. Appl. No. 10/816,072, filed Mar. 31, 2004, Dugan et al.
U.S. Appl. No. 10/824,754, filed Apr. 15, 2004, Perng.
U.S. Appl. No. 10/833,902, filed Apr. 27, 2004, Chen et al.
U.S. Appl. No. 10/835,229, filed Apr. 28, 2004, Prabhu et al.
U.S. Appl. No. 10/835,656, filed Apr. 30, 2004, Hossainy et al.
U.S. Appl. No. 10/851,411, filed May 20, 2004, Chen.
U.S. Appl. No. 10/855,294, filed May 26, 2004, Pacetti et al.
Angioplasty.org., *Balloons and Stents*, http://www.ptca.org/devices04.html, printed Oct. 15, 2004, 2 pages.
Anonymous, *Capillary Action*, http://www.ndt-ed.org/EducationResources/CommunityCollege/PenetrantTest/Introduction/Keywords/pt1.htm, printed Aug. 12, 2005, 1 page.
Anonymous, *Capillary Force Lithography (CFL)*, Nano Processing and Organic Devices Lab, 2 pages, no date.

Anonymous, *Capillary Rise of Liquid in Different Vanes Under Variable Residual Acceleration*, http://www.zarm.uni-bremen.de/2forschung/grenzph/isoterm/cap_rise/kapst_en.htm, ZARM—University of Bremen, printed Jun. 25, 2003, 2 pages.
Anonymous, *Cardiologists Draw—Up The Dream Stent*, Clinica 710, pp. 15 (Jun. 17, 1996), http://www.dialogweb.com/cgi/document?reg=1061848202959, printed Aug. 25, 2003, 2 pages.
Anonymous, *Coating Techniques, Air Knife Coating*, http://www.ferron-magnetic.co.uk/coatings/airknife.htm, printed Jul. 1, 2003, 1 page.
Anonymous, *Coating Techniques, Gap Coating (Knife Over Roll, etc.)*, http://www.ferron-magnetic.co.uk/coatings/knife.htm, printed Jul. 1, 2003, 1 page.
Anonymous, *Coating Techniques, Gravure Coating*, http://www.ferron-magnetic.co.uk/coatings/gravure.htm, printed Jul. 1, 2003, 2 pages.
Anonymous, *Coating Techniques, Reverse Roll Coating*, http://www.ferron-magnetic.co.uk/coatings/revroll.htm, printed Jul. 1, 2003, 22 pages.
Anonymous, *Heparin-coated stents cut complications By 30%*, Clinica 732, pp. 17 (Nov. 18, 1996), http://www.dialogweb.com/cgi/document?reg=1061847871753, printed Aug. 25, 2003, 2 pages.
Anonymous, *Liquid Gravity Motor*, http://w ww.drspark86.com/idea001.html, printed Jun. 24, 2003, 2 pages, no date.
Anonymous, *Porosimetry—Why characterize the porosity?* 42 pages, no date.
Anonymous, *Rolling Therapeutic Agent Loading Device for Therapeutic Agent Delivery or Coated Stent* (Abstract 434009), Res. Disclos. pp. 974-975 (Jun. 2000).
Anonymous, *Stenting Continues to Dominate Cardiology*, http://www.dialogweb.com/cgi/document?reg=1061848017752, Clinica vol. 720, pp. 22 (Sep. 2, 1996), printed Aug. 25, 2003, 2 pages.
Anonymous, *Surface Energy (Surface Wetting Capability)*, http://www.ndt-ed.org/EducationResources/CommunityCollege/PenetrantTest/PTMaterials/surfaceenergy.htm, printed Apr. 6, 2004, 3 pages, no date.
Anonymous, *The 14th International Young Physicists Tournament, The winning report*, Research Center for Quantum Information, Slovak Academy of Sciences, 5 pages, no date.
Anonymous, *The Wicking Well System*, http://www.decorative.com/wicking.html, printed Jun. 24, 2003, 1 page.
Anonymous, *Typical Parylene Properties*, 3 pages, no date.
Anonymous, *Viscosity*, Commonwealth of Australia, 7 pages, no date.
Ansari, *End-to-End Tubal Anastomosis Using an Absorbable Stent*, Fertility and Sterility, vol. 32, No. 2, pp. 197-201 (Aug. 1979).
Ansari, *Tubal Reanastomosis Using Absorbable Stent*, International Journal of Fertility, vol. 23, No. 4, pp. 242-243 (1978).
Aoyagi et al., *Preparation of cross-linked aliphatic polyester and application to thermo-reponsive material*, Journal of Controlled Release 32, pp. 87-96 (1994).
Barath et al., *Low Dose of Antitumor Agents Prevents Smooth Muscle Cell Proliferation After Endothelial Injury*, JACC vol. 3, No. 2, pp. 252A (Feb. 1989).
Barbucci et al., *Coating of commercially available materials with a new heparinizable Material*, Journal of Biomedical Materials Research, vol. 25, pp. 1259-1274 (1991).
Beach et al., *Xylylene Polymers*, Encyclopedia of Polymer Science and Engineering, vol. 17, 2nd Edition, pp. 990-1025 (1989).

Boston Scientific, *Express 2™ Coronary Stent System*, http://www.bostonscientific.com/med_specialty/deviceDetail.jsp?task=tskBasicDevice.jsp&sectionId=4&relId=2,74,75,76&deviceId=11001&uniqueId=MPDB1180&clickType=endeca, printed Aug. 8, 2005, 1 page.

Bull, *Parylene Coating for Medical Applications*, Medical Product Manufacturing News, 2 pages (Mar. 1993).

Casper et al., *Fiber-Reinforced Absorbable Composite for Orthopedic Surgery*, Polymeric Materials Science and Engineering, vol. 53, pp. 497-501(1985).

Charlson et al., *Temperature Selective Deposition of Parylene-C*, IEEE Transactions of Biomedical Engineering, vol. 39, No. 2, pp. 202-206 (Feb. 1992).

Chen et al., *The Kinetics of Wicking of Liquid Droplets into Yarns*, submitted to the Textile Research Journal, pp. 1-30 (Apr. 2001).

Chung et al., *Inner core segment design for drug delivery control of thermo-responsive polymeric micelles*, Journal of Controlled Release, vol. 65, pp. 93-103 (2000).

Crowe et al., *Absorption and Intestinal Metabolism of SDZ-RAD and Rapamycin in Rats*, Drug Metabolism and Disposition, vol. 27, No. 5, pp. 627-632 (1999).

De Scheerder et al., *Biocompatibility of polymer-coated oversized metallic stents implanted in normal porcine coronary arteries*, Atherosclerosis, vol. 114, pp. 105-114 (1995).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9, No. 2, pp. 111-130 (Mar. /Apr. 1996).

Detweiler et al., *Sliding, Absorbable, Reinforcement Ring and an Axially Driven Stent Placement Device for Sutureless Fibrin Glue Gastrointestinal Anastomisis*, Journal of Investigative Surgery, vol. 9, No. 6, pp. 495-504 (Nov./Dec. 1996).

Detweiler et al., *Sutureless Anastomosis of the Small Intestine and the Colon in Pigs Using an Absorbable Intraluminal Stent and Fibrin Glue*, Journal of Investigative Surgery, vol. 8, No. 2, pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9, No. 1, pp. 13-26 (Jan./Feb. 1996).

Dev et al., *Kinetics of Drug Delivery to the Arterial Wall Via Polyurethane-Coated Removable Nitinol Stent: Comparative Study of Two Drugs*, Catheterization and Cardiovascular Diagnosis, vol. 34, pp. 272-278 (1995).

Devanathan et al., *Polymeric Conformal Coatings for Implantable Electronic Devices*, IEEE Transactions on Biomedical Engineering, vol. BME-27, No. 11, pp. 671-675 (1980).

Dichek et al., *Seeding of Intravascular Stents with Genetically Engineered Endothelial Cells*, Circulation, vol. 80, No. 5, pp. 1347-1353 (Nov. 1989).

Dreyer et al., *Critical Velocities in Open Capillary Flows*, pp. 604-609, no date.

Duerig et al., *A comparison of balloon-and self-expanding stents*, Min. Invas. Ther. & Allied Technol., vol. 11, No. 4, pp. 173-178 (2002).

Dutkiewicz, *Some Advances in Nonwoven Structures for Absorbency, Comfort and Aesthetics*, AUTEX Research Journal, vol. 2, No. 3, pp. 153-165 (Sep. 2002).

EFD, *780S Series Spray Valves VALVEMATE™ 7040 Controller Operating Manual*, 24 pages (2002).

Eigler et al., *Local Arterial Wall Drug Delivery from a Polymer Coated Removable Metallic Stent: Kinetics, Distribution, and Bioactivity of Forskolin*, JACC, vol. 4A, pp. 701-701, Abstract (Feb. 1994).

Elbert et al., *Conjugate Addition Reactions Combined with Free-Radical Cross-Linking for the Design of Materials for Tissue Engineering*, Biomacromolecules, vol. 2, pp. 430-441 (2001).

Erickson et al., *Numerical Simulations of Capillary-Driven Flows in Nonuniform Cross-Sectional Capillaries*, Journal of Colloid and Interface Science, vol. 250, pp. 422-430 (2002).

Eskin et al., *Growth of Cultured Calf Aortic Smooth Muscle Cells on Cardiovascular Prosthetic Materials*, J. Biomed. Mater. Res. vol. 10, pp. 113-122 (1976).

Eskin et al., *Tissue Cultured Cells: Potential Blood Compatible Linings for Cardiovascular Prostheses*, Polymer Science and Technology, vol. 14, pp. 143-161, no date.

Fischell et al., *Low-Dose, β -Particle Emission from 'Stent' Wire Results in Complete, Localized Inhibition of Smooth Muscle Cell Proliferation*, Circulation, vol. 90, No. 6, pp. 2956-2963 (Dec. 1994).

Fischell et al., *The Bx VELOCITY™ STENT*, 5 pages, Biocompatibles Ltd. (2001).

Gengenbach et al., *Evolution of the Surface Composition and Topography of Perflurinated Polymers Following Ammonia-Plasma Treatment*, Plasma Surface Modifications of Polymers, pp. 123-146 (1994).

Gercken et al., *Results of the Jostent Coronary Stent Graft Implantation in Various Clinical Settings: Procedural and Follow-Up Results*, vol. 56, No. 3, pp. 353-360 (2002).

Gölander et al., *RF-Plasma-Modified Polystyrene Surfaces for Studying Complement Activation*, J. Biomater. Sci. Plymer Edn., vol. 4, No. 1 pp. 25-30 (1992).

Guidant, *ACS RX MULTI-LINK™ Coronary Stent System*, 6 pages, no date.

Guidant, *Guidant MULTI-LINK Vision OTW Coronary Stent System*, 2 pages, no date.

Hahn et al., *Biocompatibility of Glow-Discharge-Polmerized Films and Vacuum-Deposited Parylene*, Journal of Applied Polymer Science: Applied Polymer Symposium 38, 55-64 (1984).

Hahn et al., *Glow Discharge Polymers as Coatings for Implanted Devices*, John M. Dalton Research Center, University of Missouri-Columbia and the Graduate Center for Materials Research, pp. 109-113 (1981).

He et al., *Assessment of Tissue Blood Flow Following Small Artery Welding with an Intraluminal Dissolvable Stent*, Microsurgery, vol. 19, No. 3, pp. 148-152 (1999).

Hehrlein et al., *Low-Dose Radioactive Endovascular Stents Prevent Smooth Muscle Cell Proliferation and Neointimal Hyperplasia in Rabbits*, Circulation, vol. 92, No. 6, pp. 1570-1575 (Sep. 15, 1995).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol., vol. 3, pp. 197-199 (1998).

Hollahan et al., *Attachment of Amino Groups to Polymer Surfaces by Radiofrequency Plasmas*, Journal of Applied Polymer Science, vol. 13, pp. 807-816 (1969).

Huang et al., *Biodegradable Polymers Derived from Aminoacids*, Macromol. Symp. 144, 7-32 (1999).

Impulse Jetting, *About Us*, http://www.impulsejetting.com/about.html, printed Dec. 18, 2000, 1 page.

Impulse Jetting, *Our Technology*, http://www.impulsejetting.com/tech1.html, printed Dec. 18, 2000, 1 page.

Inagaki et al., *Hydrophilic Surface Modification of Polyethylene by No-Plasma Treatment*, Adhesion Sci. Technol., vol. 4, No. 2, pp. 99-107 (1990).

Inoue et al., *An AB block copolymer of oligo(methyl methacrylate) and poly(acrylic acid) for micellar delivery of hydrophobic drugs*, Journal of Controlled Release, vol. 51, pp. 221-229 (1998).

Itabashi et al., *Electroless Deposited CoWB for Copper Diffusion Barrier Metal*, International Interconnect Technology Conference, pp. 285-287 (2002).

John Ritchie Production Group, *Production of Stents* (presentation), 15 pages (Apr. 24, 2003).

Kataoka et al., *Block Copolymer Micelles as Vehicles for Drug Delivery*, Journal of Controlled Release vol. 24, pp. 119-132 (1993).

Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, vol. 37, 391-407 (1999).

Kawai et al., *Physiologically Based Pharmacokinetics of Cyclosporine A: Extension to Tissue Distribution Kinetics in Rats and Scale-up to Human*, The Journal of Pharmacology and Experimental Therapeutics, vol. 287, No. 2, pp. 457-468 (1998).

Kelley et al., *Totally Resorbable High-Strength Composite Material*, Advances in Biomedical Polymers, vol. 35, pp. 75-85 (1987).

Klocke et al, *How Soil Holds Water* (G90-964), http://ianrpubs.unl.edu/fieldcrops/g964.htm, printed Apr. 6, 2004, 9 pages.

Konopka, *In-Plane Moisture Transport in Nonwovens*, Nonwovens Cooperative Research Center, NC State University, 56 pages.

Kovarik et al., *Pharmacokinetic and Pharmacodynamic Assessments of HMG-CoA Reductase Inhibitors When Coadministered with Everolimus*, Journal of Clinical Pharmacology, vol. 42, pp. 222-228 (2002).

Kubies et al., *Microdomain Structure In polylactide-block-poly(ethylene oxide) copolymer films*, Biomaterials, vol. 21, pp. 529-536 (2000).

Kutryk et al., *Coronary Stenting: Current Perspectives, a companion to the Handbook of Coronary Stents*, 16 pages (1999).

Lambert et al., *Localized Arterial Wall Drug Delivery From a Polymer-Coated Removable Metallic Stent*, Circulation, vol. 90, No. 2, pp. 1003-1011 (Aug. 1994).

Lemos et al., *Coronary Restenosis After Sirolimus-Eluting Stent Implantation*, Circulation, vol. 108, No. 3, pp. 257-260 (Jul. 22, 2003).

Levy et al., *Strategies For Treating Arterial Restenosis Using Polymeric Controlled Release Implants*, Biotechnology and Bioactive Polymers, pp. 259-268 (1994).

Liermann et al., *Prophylactic Endovascular Radiotherapy to Prevent Intimal Hyperplasia after Stent Implantation in Femoropopliteal Arteries*, CardioVascular and Interventional Radiology, vol. 17, pp. 12-16 (1994).

Liu et al., *Drug Release Characteristics of Unimolecular Polymeric Micelles*, Journal of Controlled Release, vol. 68, pp. 167-174 (2000).

Loeb et al., *Parylene as a Chronically Stable, Reproducible Microelectrode Insulator*, IEEE Transactions on Biomedical Engineering, Mar. 1997 (pp. 121-128).

Loh et al., *Plasma Enhanced Parylene Deposition*, Antec, pp. 1099-1103, 1991.

Machine Solutions, *FFS700 MSI Balloon Form/Fold/Set Equipment (PTCA), FFS800 MSI Balloon Form/Fold/Set Equipment (PTA)*, http://machinesolutions.org/ffs7_8.html, printed Nov. 21, 2003 (2 pgs.).

Machine Solutions, *SC700 MSI Stent Crimping Equipment (PTCA), SC800 MSI Stent Crimping Equipment (PTA)*, http://www.machinesolutions.org/sc7_8.html, printed Nov. 21, 2003, 2 pages.

Malik et al., *Development of an Energetic Ion Assisted Mixing and Deposition Process for $TIN_x$ and Diamondlike Carbon Films, Using a Co-axial Geometry in Plasma Source Ion Implantation*, J. Vac. Sci. Technol. A, vol. 15, No. 6, pp. 2875-2879 (Nov./Dec. 1997).

Malik et al., *Overview of plasma source ion implantation research at University of wisconsin-Madison*, J. Vac. Sci. Technol. B, No. 12, vol. 2, pp. 843-849 (Mar./Apr. 1994).

Malik et al., *Sheath dynamics and dose analysis for planar targets in plasma source ion implantation*, Plasma Sources Sci. Technol. vol. 2, pp. 81-85 (1993).

Marconi et al., *Covalent bonding of heparin to a vinyl copolymer for biomedical applications*, Biomaterials, vol. 18, No. 12, pp. 885-890 (1997).

Martin et al., *Enhancing the biological activity of immobilized osteopontin using a type-1 collagen affinity coating*, J. Biomed. Mater. Res., vol. 70A, pp. 10-19 (2004).

Matsumaru et al., *Embolic Materials For Endovascular Treatment of Cerebral Lesions*, J. Biomater. Sci. Polymer Edn., vol. 8, No. 7, pp. 555-569 (1997).

Mauduit et al., *Hydrolytic degradation of films prepared from blends of high and low molecular weight poly(DL-lactic acid)s*, J. Biomed. Mater. Res., vol. 30, pp. 201-207 (1996).

Middleton et al., *Synthetic biodegradable polymers as orthopedic devices*, Biomaterials, vol. 21, pp. 2335-2346 (2000).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull., vol. 33, No. 6, pp. 2490-2498 (1985).

Miyazawa et al., *Effects of Pemirolast and Tranilast on Intimal Thickening After Arterial Injury in the Rat*, J. Cardiovasc. Pharmacol., vol. 30, No. 2, pp. 157-162 (1997).

Moody, *Vacuum Coating Ultrasonic Transducers*, 1 page, Sensors (Dec. 1993).

Muller et al., *Advances in Coronary Angioplasty: Endovascular Stents*, Coronary Artery Disease, vol. 1, No. 4., pp. 438-448 (Jul./Aug. 1990).

Neimark et al., *Hierarchical Pore Structure and Wetting Properties of Single-Wall Carbon Nanotube Fibers*, Nano Letters, vol. 3, No. 3, pp. 419-423 (2003).

Nichols et al., *Electrical Insulation of Implantable Devices by Composite Polymer Coatings*, ISA Transactions, vol. 26, No. 4, pp. 15-18 (1987).

Nordrehaug et al., *A Novel Biocompatible Coating Applied to Coronary Stents*, EPO Heart Journal 14, p. 321 (P1694), Abstr. Suppl. (1993).

Nova Tran™ Custom Coating Services, *Parylene Conformal Coating*, 8 pages, no date.

Ohsawa et al., *Preventive Effects of an Antiallergic Drug, Pemirolast Potassium, on Restenosis After Percutaneous Transluminal Coronary Angioplasty*, American Heart Journal, vol. 136, No. 6, pp. 1081-1087 (Dec. 1998).

Olson, *Parylene, a Biostabel Coating for Medical Applications,* Specialty Coating Systems, Inc. Nova Tran™ Parylene Coating Services, no date.

Ozaki et al., *New Stent Technologies,* Progress in Cardiovascular Diseases, vol. XXXIX, No. 2, pp. 129-140 (Sep./Oct. 1996).

Para Tech Coating Company, *Galxyl, Parylene Coatings by Para Tech,* 1 page, no date.

Para Tech Coating Company, *Lab Top® Parylene Deposition System,* 2 pages, no date.

Pechar et al., *Poly(ethylene glycol) Multiblock Copolymer as a Carrier of Anti-Cancer Drug Doxorubicin,* Bioconjucate Chemistry vol. 11, No. 2, pp. 131-139 (Mar./Apr. 2000).

Peng et al., *Role of polymers in improving the results of stenting in coronary arteries,* Biomaterial, vol. 17, pp. 685-694 (1996).

Peuster et al., *A novel approach to temporary stenting: degradable cardiovascular stents produced from corrodible metal-results 6-18 months after implantation into New Zealand white rabbits,* Heart vol. 86, pp. 563-569 (2001).

Pietrzak et al., *Bioabsorbable Fixation Devices: Status for the Craniomaxillofacial Surgeon,* Journal of Craniofacial Surgery, vol. 8, No. 2, pp. 92-96 (1997).

Pietrzak et al., *Bioresorbable Implants—Pratical Considerations,* Bone, vol. 19, No. 1, Supplement, pp. 109S-119S (Jul. 1996).

Poncin-Epaillard et al., *Reactivity of a Polypropylene Surface Modified in a Nitrogen Plasma,* Plasma Surface Modification of Polymers pp. 167-180 (1994).

Prabhu, *Computational Modeling in Stent-based Drug Delivery,* Business Briefing: Medical Device Manufacturing & Technology, 4 pages (2004).

Redman, *Clinical Experience with Vasovasostomy Utilizing Absorbable Intravasal Stent,* Urology, vol. XX, No. 11, pp. 59-61 (Jul. 1982).

Refracton Techonolgies, Corp., *Fine Bubble Diffusers,* 2 pages, do date.

Refracton Techonolgies, Corp., *Refractron Advanced Porous Ceramic Product Capabilities,* http://www.refractron.com/ecom/sp/cat=Product+Information, printed Apr. 6, 2004, 3 pages.

Refracton Technologies Corp., http://www.refractron.com/ecom/sp/cat=Custom+Applications, printed Jun 24, 2003, 1 page.

Rust et al., *The Effect of Absorbable Stenting on Postoperative Stenosis of the Surgically Enlarged Maxillary Sinus Ostia in a Rabbit Animal Model,* Archives of Otolaryngology, Head and Neck Surgery, vol. 122, pp. 1395-1397 (Dec. 1996).

Sadhir et al., *The Adhesion of Glow-Discharge Polymers, Silastic And Parylene to Implantable Platinum Electrodes: Results of Tensil Pull tests After Exposure to Isotonic Sodium Chloride,* Biomaterials, vol. 2, pp. 239-243 (Oct. 1981).

Saotome, et al., *Novel Enzymatically Degradable Polymers Comprising α-Amino Acid, 1,2-Ethanediol, and Adipic Acid,* Chemistry Letters, pp. 21-24, (1991).

Schatz, *A View of Vascular Stents,* Circulation, vol. 79, No. 2, pp. 445-457 (Feb. 1989).

Scheuer et al., *Model of plasma source ion implantation in planar, cylindrical, and spherical geometries,* J. Appl. Phys., vol. 67, No. 3, pp. 1241-1245 (Feb. 1990).

Schmidt et al., *Long-term Implants of Parylene-C Coated Microelectrodes,* Medical & Biological Engineering & Computing, pp. 96-101 (Jan. 1988).

Serkova et al., *Tissue Distribution and Clinical Monitoring of the Novel Macrolide Immunosuppressant SDZ-RAD and its Metabolites in Monkey Lung Transplant Recipients: Interaction with Cyclosporine,* The Journal of Pharmacology and Experimental Therapeutics, vol. 294, No. 1, pp. 323-332 (2000).

Serruys et al., *I Like the Candy, I Hate the Wrapper; the $^{32}P$ Radioactive Stent,* Circulation, vol. 101, pp. 3-7 (Jan. 2000).

Shamim et al., *Measurement of electron emission due to energetic ion bombardment in plasma source ion implantation,* J. Appl. Phys., vol. 70, No. 9, pp. 4756-4759 (Nov. 1991).

Shamim et al., *Measurements of Spatial and Temporal Sheath Evolution for Spherical and Cylindrical Geometries in Plasma Source Ion Implantation,* J. Appl. Phys., vol. 69, No. 5, pp. 2904-2908 (Mar. 1991).

Shigeno, *Prevention of Cerebrovascular Spasm By Bosentan, Novel Endothelin Receptor,* Chemical Abstract 125:21230 (1996).

Sono Tek Corporation, *AccuMist™ for Single Stent Coating Applications,* http://www.sono-tek.com/biomedical/accumist_stent.html, printed Aug. 2, 2005, 3 pages.

Sono Tek Corporation, *MediCoat™ DES 1000, Benchtop Stent Coating System,* http://www.sono-tek.com/biomedical/medicoat_standalone.html, printed Aug. 2, 2005, 4 pages.

Sono Tek Corporation, *MicroMist for Stent Coating,* http://www.sono-tek.com/biomedical/micromist_stent.html, printed Aug. 2, 2005, 3 pages.

Spagnuolo et al., *Gas 1 is induced by VE-cadherin and vascular endothelial growth factor and inhibits endothelial cell apoptosis,* Blood, vol. 103, No. 6, pp. 3005-3012 (2004).

Specialty Coating Systems, Inc., *The Parylene Press,* 4 pages (Summer 1993).

Specialty Coating Systems, Inc., *The Parylene Press,* 6 pages (Spring 1993).

Specialty Coating Systems, Inc., *The Parylene Press,* 7 pages (Winter 1992).

Specialty Coating Systems, *Parylene and Nova Tran™ Parylene Coating Services, for Unmatched Conformal Coating Performance,* 21 pages, no date.

Specialty Coating Systems, *Parylene, a Biostable Coating for Medical Applications,* 6 pages, no date.

Specialty Coating Systems, *Repair and Recoating of Parylene Coated Printed Circuit Boards,* 15 pages, no date.

Straube, *Moisture, Materials, & Buildings,* HPAC Engineering, pp. 2-7, no date.

Taher, *Capillary interaction between a small thin solid plate and a liquid,* Mechanical and Industrial Engineering, University of Illinois at Urbana-Champaign, 4 pages, undated.

Tamai et al., *Initial and 6-Month Result of Biodegradable Poly-I-Lactic Acid Coronary Stents in Humans,* Circulation, vol. 102, pp. 399-404 (2000).

Trident, Inc., http://www.tridentintl.com/subbody.html, printed Dec. 18, 2000, 1 page.

Trident, Inc., *Product Lines,* http://www.tridentintl.com/products-apps/ultrajet.html, printed Dec. 18, 2000, 3 pages.

Tsuji et al., *Biodegradable Polymeric Stents,* Current Interventional Cardiology Reports vol. 3, pp. 10-17 (2001).

Union Carbide Adhesion Promoters, *Union Carbide A-174 Silane,* 5 pages (Jan. 1968).

Union Carbide Electronics Division, *Parylene Environmentally Compatible Conformal Coatings for Electronic Components Assemblies and Precision Parts,* 14 pages, no date.

Union Carbide, *Abrasion Resistance of Parylene and Other*

*Conformal Circuit Board Coatings*, Parylene Products, No. 4, 13 pages (Oct. 1977).
Union Carbide, *Adhesion Promotion Systems for Parylene*, Parylene Products, No. 15, Revision 1, 8 pages (Oct. 1977).
Union Carbide, *Adhesion Promotion Systems for Parylene*, Technology Letter, No. 15, 13 pages (Oct. 1975).
Union Carbide, *Evaluation of Parylene and Other Pellicles as Beam Splitters*, Parylene Products, No. 8, Edited, 19 pages (Oct. 1977).
Union Carbide, *Fluorescent Parylene Coatings*, Parylene Products, No. 7, Revision 1, 8 pages (Oct. 1977).
Union Carbide, *Fluorescent Parylene Coatings*, Technology Letter, No. 7, 8 pages (Oct. 1973).
Union Carbide, *Mechanical Protection Criteria for Thin Conformal Coatings*, Parylene Products, No. 3, 21 pages (Oct. 1977).
Union Carbide, *Method for Repair and Patching of Parylene Coated Printed Circuit Boards*, Parylene Products, No. 2 Revision 1, 9 pages (Oct. 1977).
Union Carbide, *Microencapsulation by Vapor Deposition*, Parylene Products, No. 6, 12 pages (Oct. 1977).
Union Carbide, *MIL I 46058, Qualification of Parylene N, C, and D*, Parylene Products, No. 1, Revision 2, 8 pages (Oct. 1977).
Union Carbide, *Parylene Bibliography*, Parylene Products, No. 5, Revision 4, 17 pages (Jan 18, 1982).
Union Carbide, *Parylene Conformal Coatings for Hybrid Microelectronics*, Parylene Products, No. 9, 23 pages (Oct. 1973).
Union Carbide, *Parylene Pellicles for Space Applications*, Parylene Products, No. 10, 50 pages (Oct. 1977).
Union Carbide, *Parylene Pyrolysis Kinetics*, Parylene Products, No. 11, 12 pages (Oct. 1977).
Union Carbide, *Parylene Pyrolysis Kinetics*, Technology Letter, No. 11, 12 pages (May 1974).
Union Carbide, *Parylene Removal with Oxygen Plasmas*, Parylene Products, No. 18, 7 pages (Aug. 1977).
Union Carbide, *Printed Circuit Board Masking Techniques for Use with Parylene*, No. 14, Revision 1, 11 pages (Oct. 1977).
Union Carbide, *Solvent Resistance of the Parylenes*, Parylene Products, No. 12, Revision 1, 5 pages (Oct. 1977).
Union Carbide, *The Selective Removal of Parylene by Plasma Etching*, No. 13, Revision 1, 7 pages (Oct. 1977).
Union Carbide, *Thermal Endurance of the Parylenes in Air*, Parylene Products, No. 16, 4 pages (Mar. 1976).
Union Carbide, *Vapor Phase Adhesion Promotion Systems*, Parylene Products, No. 17, Revision 1, 11 pages (Oct. 1977).
van Beusekom et al., *Coronary Stent Coatings*, Coronary Artery Disease, vol. 5, No. 7, pp. 590-596 (Jul. 1994).
van der Giessen et al., "Edge Effect" of $^{32}P$ *Radioactive Stents is Caused by the Combination of Chronic Stent Injury and Radioactive Dose Falloff*, Circulation, vol. 104, pp. 2236-2241 (Oct. 30, 2001).
Vapor Inc., *Vapore-Jet™ Capillary Pump—How it Works*, http://www.vapore.com/tech_howto.htm, printed Aug. 13, 2003, 2 pages.
Völkel et al., *Targeting of immunoliposomes to endothelial cells using a single-chain Fv fragment directed against human endoglin (CD105)*, Biochemica et Biophysica Acta, vol. 1663, pp. 158-166 (2004).
von Recum et al., *Degradation of polydispersed poly(L-lactic acid) to modulate lactic acid release*, Biomaterials, vol. 16, pp. 441-445 (1995).
Wiesendanger et al., *Contributions of Scanning Probe Microscopy and Spectroscopy to the Investigation and Fabrication of Nanometer-Scale Structures*, J. Vac. Sci. Technol. B, vol. 12, No. 2, pp. 515-529 (Mar./Apr. 1994).
Wilensky et al., *Methods and Devices for Local Drug Delivery in Coronary and Peripheral Arteries*, Trends Cardiovasc. Med., vol. 3, No. 5, pp. 163-170 (1993).
Wong et al., *An Update on Coronary Stents*, Cardio, 8 pages (Feb. 1992).
World Precision Instruments, Inc., http://www.wpiinc.com/WPI_Web/Pumps/pneumatic_Fig.gif, printed Sep. 20, 2002, 1 page.
World Precision Instruments, Inc., *Nanoliter Injector*, http://www.wpiinc.com/WPI_Web/Microinjection/Nanoliter_Injector.html, printed Jun. 10, 2005, 3 pages.
World Precision Instruments, Inc., *Nanoliter Injector*, http://www.wpi-europe.com/products/microinjection/nanoliter.htm printed Jun. 10, 2005, 2 pages.
World Precision Instruments, Inc., *Pneumatic PicoPumps*, http://www.wpieurope.com/products/microinjection/picopumps.htm, printed Jun. 10, 2005, 4 pages.
World Precision Instruments, Inc., *Pneumatic PicoPumps*, http://www.wpiinc.com/WPI_Web/Microinjection/Pneumatic_PicoPumps.html, printed Jun. 10, 2005, 4 pages.
Yau et al., *Modern Size-Exclusion Liquid Chromatography*, Wiley-Interscience Publication, 9 pages (1979).
Yokoyama et al., *Characterization of physical entrapment and chemical conjugation of adriamycin in polymeric micelles and their design for in vivo delivery to asolid tumor*, Journal of Controlled Release, vol. 50, pp. 79-92 (1998).
Yuen et al., *Tissue response to potential neuroprosthetic materials implanted subdurally*, Biomaterials, vol. 8, pp. 57-62 (Mar. 1987).
Zhmud et al., *Dynamics of Capillary Rise*, Journal of Colloid and Interface Science, vol. 228, pp. 263-269 (2000).
Zimarino et al., *Analysis of Stent Edge Restenosis with Different Forms of Brachytherapy*, The American Journal of Cardiology, vol. 89, pp. 322-325 (Feb. 1, 2002).
Zylberman et al., *Comparative Study of Electroless Co(W,P) and Co(Mo,P) Thin-Films for Capping and Barrier Layers for Cu Metallization*, 2002 Advanced Metallization Conference, 2 pages, no date.

* cited by examiner

METHOD OF REDUCING OR ELIMINATING THROMBUS FORMATION

CROSS REFERENCE

This is a divisional of application Ser. No. 08/847,763 filed on Apr. 24, 1997 now U.S. Pat. No. 6,776,792.

BACKGROUND OF THE INVENTION

The present invention relates to endovascular stents and more particularly pertains to coatings that are applied to stents in order to reduce thrombogenicity.

Stents are implanted within blood vessels in an effort to maintain their patency by preventing collapse of the lumen and/or by impeding restenosis. Unfortunately, the presence of a foreign object within the blood flow may have a thrombogenic effect. It has therefore been found to be desirable to use various anti-coagulant drugs in an effort to reduce the likelihood of the development of restenosis and provide an antithrombogenic effect.

A drug that has been found to be particularly effective for such purpose is heparin. By maintaining an effective concentration of the drug in and about the implantation site until the stent is encapsulated by tissue, the risk of thrombogenesis is substantially mitigated. To that end, various approaches have been employed in the administration of heparin.

While the systemic administration of heparin can cause the implantation site to be subjected to an effective level of heparin, such level of heparin would necessarily also be present throughout the rest of the body which can lead to undesirable side effects such as bleeding. It has therefore been recognized that a regimen wherein the heparin is substantially constrained to the implantation site is far more desirable. An approach that has been devised to achieve such end requires the coating or impregnation of the stent itself with heparin. The heparin is thereby concentrated where it is most needed while its presence, and consequently its effect, throughout the rest of the body is minimized.

Disadvantages associated with heretofore known heparinized stents include, the limited shelf life of such devices, the fact the heparin is degraded when the stent is sterilized either by heat or by exposure to ethylene dioxide, the inability of the physician to alter the dosage that the patient is subjected to and the inability to replenish any heparin that may be lost while the device is deployed. Additionally, the cost of heretofore known heparinized stent devices has been very high as it necessarily includes the costs associated with the stringent regulatory requirements attendant a drug containing device.

The prior art has been unable to overcome these disadvantages and shortcomings and a new approach is needed to safely, effectively, and economically deliver heparin to an implantation site.

SUMMARY OF THE INVENTION

The present invention provides for the coating of an implantable endovascular device to facilitate the subsequent loading of heparin onto its surface. Such loading can be achieved in vitro just prior to implantation or preferably, in vivo after the device is in place. As a result, the device has a considerably longer shelf-life than heparin-containing devices, the need for special handling and sterilization procedures associated with heparin-containing devices is obviated, and the dosage of heparin can be readily tailored to an individual patient's needs including any adjustment that may be required after the device has been deployed. An additional advantage provided by such a device is that it is not subject to the stringent regulatory requirements associated with drug-containing devices.

More particularly, the present invention provides for the coating of stent surfaces with a material or combination of materials that are selected for their ability to adhere to the stent surface, to attract heparin and to form preferably an ionic bond therewith. The heparin is attracted by and attaches to functional groups incorporated in the coating which may include primary, secondary, and/or tertiary amines or other functionalities such as carboxyl groups.

The heparin-attracting coating may be applied so as to encapsulate the entire stent or alternatively, to cover only selected surfaces thereof. By limiting coverage to only the inner surface of the stent, i.e., the surface that is directly exposed to blood flow, a much higher level of heparin can be loaded onto the stent than would be safe if such level were in direct contact with the vessel wall. A toxic effect on the vessel wall is thereby avoided while the blood is exposed to a more effective concentration of heparin. Alternatively, it may be deemed sufficient to coat only the ends of the stent, i.e., where disturbance of flow is greatest and where thromboses are most likely to occur.

The coating may be applied by different processes such as by dipping, spraying or molding. The preferred method is by plasma deposition wherein a base layer, selected for its ability to adhere to the stent surface, is first deposited on the stent followed by the deposition of a top layer thereon that is selected for its ability to bond to the base layer and to avail the appropriate functional groups for bonding to the heparin.

These and other features and advantages of the present invention will become apparent from the following detailed description which, taken in conjunction with the accompanying drawings, illustrates by way of example the principles of the invention.

DETAILED DESCRIPTION OF THE PREFERRED EMBODIMENTS

Figure 1:
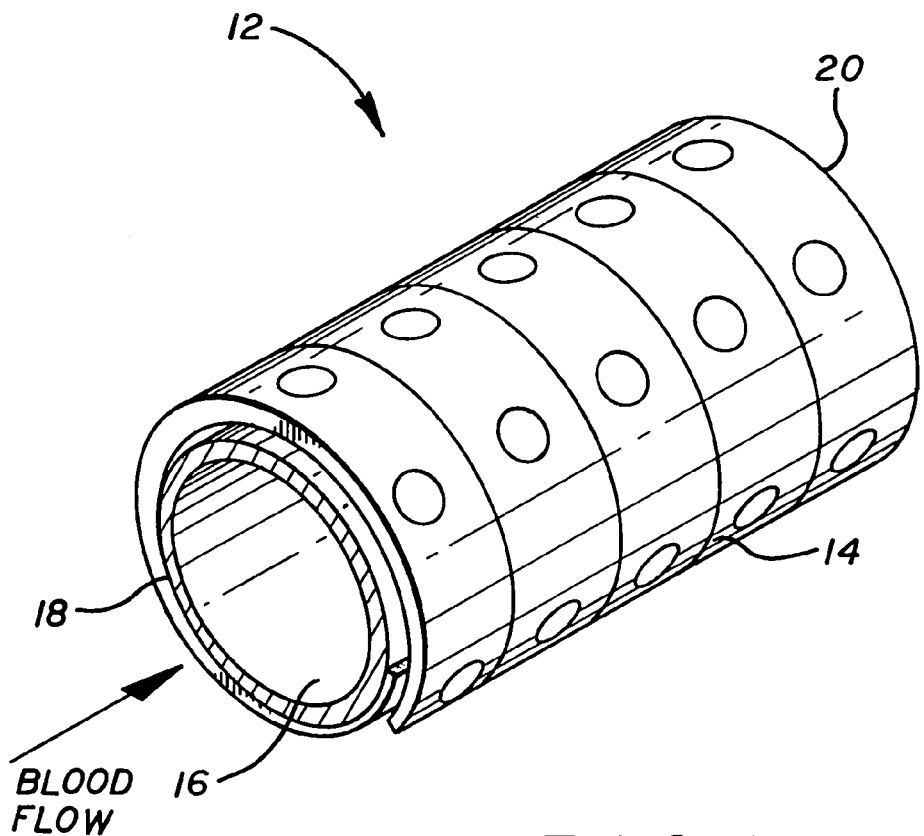
FIG. 1 is a perspective view of an implantable stent.

A wide variety of different stent configurations have been devised to address various issues inherent in their use and function. Additionally, various materials have been employed in their construction including metals and polymers. Both the degree of turbulence caused by a particular stent configuration when subjected to blood flow as well as the material from which it is constructed affects the degree of thrombogenicity associated with a particular stent device. The present invention provides a coating for such stents to which heparin becomes attached and thus serves to reduce or eliminate thrombosis formation. Moreover, the stent's coating allows the heparin to be loaded thereon immediately before the implantation procedure or after the stent is in place.

Critical requirements for the coating of the present invention include that it adheres to the stent surface and that it has functional groups that attract heparin and to which heparin bonds. Functional groups that are known to have the requisite affinity for heparin include primary, secondary, and tertiary amines wherein primary amines are preferred due to their enhanced affinity. Alternatively, carboxyl groups may be used. The functional groups must include positively charged entities that serve to attract the negatively charged entities associated with the heparin. Such attraction facilitates the formation of an ionic bond.

The coating can be applied by different processes such as by dipping, spraying, molding or by plasma deposition. Plasma deposition is preferred and first requires the deposition of a base layer or primer that prepares the surface of the stent to receive the functionality group containing substance. In the preferred embodiment, a metallic stent is first plasma deposited with methane gas leaving a film on the surface of the stent wherein the methane molecules are oriented with the carbon against the stent and the hydrogen exposed. A top layer that includes the desired functionalities is then deposited on the base layer. Such second layer may be formed by the plasma deposition of ammonia gas to leave the primary amine functional groups extending from the stent surface. Other chemicals such as alkylamine, nitrile compounds or amine containing monomers can also be used to plasma deposit amine functionalities on the surface. In the event a mixture of primary, secondary, and tertiary amines is deposited by such methods it is preferred that the primary amine constitutes a greater percentage of the mixture due to its greater affinity for heparin. Alternatively, the deposition of carboxyl functional groups can be achieved by the plasma deposition of monomers like methyl methacrylate or acrylic acid.

The resulting coating thickness should be 0.001 inch or less while a thickness less than 1 micron is preferred. Although it may be desirable to have a uniform concentration of functional groups extending from the surface, it is not critical to the function of the coating. On the other hand, a concentration of at least 54 picamoles/stent must be achieved in order to ensure that heparin becomes attached at an effective level.

The coating may be applied to the entire stent or just to selected surfaces thereon. FIG. 1 generally illustrates a stent 12 in its deployed state and serves to identify the vessel wall-facing surface 14, the blood flow-facing surface 16, its upstream edge 18, and its downstream edge 20. By coating only the surfaces facing the blood flow, a concentration of heparin can be loaded thereon that would be toxic to the vessel wall tissue if it were to be present on the surfaces in direct contact with the vessel wall. Alternatively, it may be sufficient to exclusively coat the upstream and/or downstream edges of the stent for a particular stent configuration implanted in a particular patient as thrombosis is most likely to occur at such interfaces due to turbulence induced by their presence in the blood flow.

After the coating process is completed, the coated stent is cleaned and sterilized and appropriately packaged for long-term storage. Due to the absence of any degradable drugs or substances on the stent, a fairly extended-shelf-life can be expected.

Figure 2:
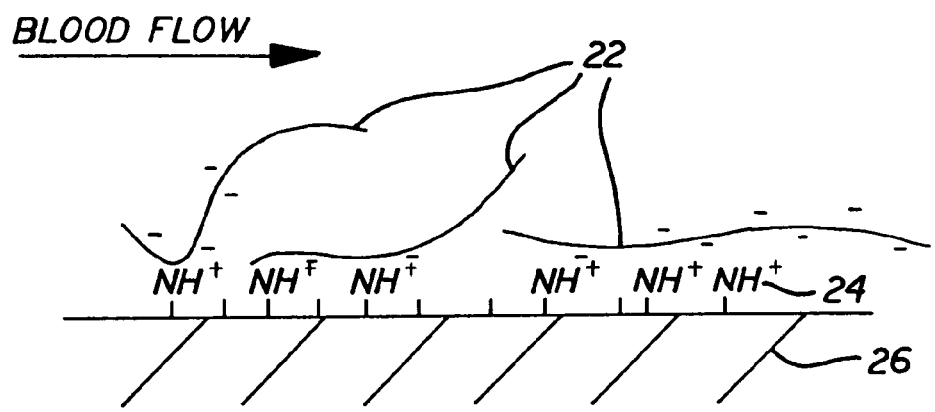
FIG. 2 is a greatly enlarged, schematic, cross-sectional view of a portion of the stent of the present invention.

The stent of the present invention can be used in two different ways. A first use calls for the stent to be implanted in the form in which it had been stored, without having heparin loaded thereon. Once in place, it is contacted with heparinized blood, either by an injection of heparin via a catheter extended to a position just upstream of the implantation site or by IV. As the heparin macromolecules 22 pass by the functional groups 24 in the coating 26, the heparin is attracted thereto and becomes attached (FIG. 2). Heparin that does not attach, quickly becomes diluted downstream of the implantation site to levels that do not adversely affect the patient. Subsequent heparin flow past the implantation site can cause more and more heparin molecules to be pulled from the blood flow until the stent coating is saturated. Once attached, heparin can inhibit coagulation by binding with anti-thrombin III and/or other factors of the coagulation cascade. Should a heparin molecule become detached, it is replaced by other heparin molecules still present in the blood flow. Alternatively, an additional dosage of heparin can be administered.

Alternatively, the physician may pre-treat the stent prior to implantation by flushing it with, for example, a heparinized saline solution. In this way, the physician can easily and precisely adjust the heparin level by controlling the concentration of the heparin in the saline solution and/or controlling the exposure time thereto. Once implanted, the heparin level can be increased or replenished by introducing heparin into the blood flow upstream of the implantation site as was described above. The heparin level is maintained on the stent until the natural healing processes cause the stent surfaces to be completely covered by tissue at which point thrombogenicity ceases to be of concern.

While a particular form of the invention has been illustrated and described, it will also be apparent to those skilled in the art that various modifications can be made without departing from the spirit and scope of the invention. Accordingly, it is not intended that the invention be limited except by the appended claims.

What is claimed is:

1. A method of reducing or eliminating a formation of a thrombus in a patient's vasculature, wherein the method comprises implanting a medical device in a patient's vasculature and allowing the medical device produced by the method comprising:
   depositing a coating devoid of heparin on the medical device that is implantable within a lumen of a vascular system; wherein,
      the lumen is defined by vessel walls;
      the medical device comprises surfaces capable of contacting the vessel walls and surfaces incapable of contacting the vessel walls upon implantation;
      the coating devoid of heparin comprises a material that deposits on the medical device and includes functional groups that attract heparin, bond with heparin, or a combination thereof, when the material is exposed to a solution comprising heparin; wherein,
      the depositing occurs exclusively on surfaces of the medical device that are incapable of contacting the vessel walls thus providing for delivery of heparin to a specific site in a patient and avoiding a toxic effect within the patient's vasculature; and
      exposing the medical device to heparinized blood such that heparin attaches to the coating exclusively on surfaces of the medical device that are incapable of contacting the vessel walls;
   to remain in the vasculature for a period of time during which the heparin attached to the coating can reduce or eliminate thrombus formation, after which period, the medical device is exposed to an additional dosage of heparin.

2. A method of reducing or eliminating a formation of a thrombus in a patient's vasculature wherein the method comprises implanting a medical device in a patient's vasculature and allowing the medical device produced by the method comprising:
   depositing a coating devoid of heparin on the medical device that is implantable within a lumen of a patient; wherein,
      the lumen is defined by vessel walls;

the medical device comprises surfaces capable of contacting the vessel walls and surfaces incapable of contacting the vessel walls upon implantation;

the coating devoid of heparin comprises a material that deposits on the medical device and includes functional groups that attract heparin, bond with heparin, or a combination thereof, when the material is exposed to a solution comprising heparin; wherein, the depositing occurs exclusively on surfaces of the medical device that are incapable of contacting the vessel walls thus providing for delivery of heparin to a specific site in a patient and avoiding a toxic effect within the patient;

sterilizing and storing the medical device having the coating deposited thereon; and exposing the coated body medical device to the solution comprising heparin, such that the heparin attaches to the coating exclusively on surfaces of the medical device that are incapable of contacting the vessel walls;

to remain in the vasculature for a period of time in which the heparin attached to the coating can reduce or eliminate thrombus formation, after which period, the medical device is exposed to an additional dosage of heparin.

3. The method of claim 1, wherein the bonding of the coating with heparin comprises ionic bonding.

4. The method of claim 1, wherein the medical device further comprises a support structure, and exposing the implantable support structure to heparinized blood comprises delivering heparin from a catheter to the patient.

5. The method of claim 4, wherein the support structure is a stent.

6. The method of claim 4, wherein the support structure is configured such that upon implantation in a blood vessel, such support structure has surfaces that face the vessel walls and surfaces that face the blood flow, wherein the surfaces of the medical device that are incapable of contacting the vessel walls comprise the surfaces that face the blood flow, and wherein the coating is exclusively deposited on the surfaces that face the blood flow.

7. The method of claim 4, wherein the support structure is configured such that upon implantation in a blood vessel, such support structure has surfaces that face the vessel walls, surfaces that face the blood flow, and end surfaces comprising an upstream edge surface and a downstream edge surface, wherein the surfaces of the medical device that are incapable of contacting the vessel walls comprise the upstream edge surface and the downstream edge surface, and wherein the coating is exclusively deposited on at least one of the end surfaces.

8. The method of claim 1, wherein the coating comprises a layer that is deposited on the medical device by dipping, spraying, molding, plasma deposition, or a combination thereof.

9. The method of claim 1, wherein the coating comprises a layer that is deposited on the medical device by plasma deposition.

10. The method of claim 1, wherein the coating is deposited by first depositing a base layer, selected for its ability to adhere to the medical device and then depositing thereon a top layer selected for its ability to bond to the base layer and avail the functional groups for attachment to the heparin.

11. The method of claim 1, wherein the functional groups comprise functional groups that are selected from a group consisting of amine groups, carboxyl groups, and a combination thereof.

12. The method of claim 2, wherein the medical device comprises a support structure.

13. The method of claim 12, wherein the support structure comprises a stent.

14. The method of claim 12, wherein the support structure is configured such that upon implantation in a patient, such support structure has surfaces that face the vessel walls and surfaces that face blood flow, wherein the surfaces of the medical device that are incapable of contacting the vessel walls comprise the surfaces that face the blood flow, and wherein the coating is exclusively deposited on the surfaces that face the blood flow.

15. The method of claim 12, wherein the support structure is configured such that upon implantation in a patient, such support structure has surfaces that face the vessel walls, surfaces that face blood flow, and end surfaces comprising an upstream edge surface and a downstream edge surface, wherein the surfaces of the medical device that are incapable of contacting the vessel walls comprise the upstream edge surface and the downstream edge surface, and wherein the coating is exclusively deposited on at least one of the end surfaces.

16. The method of claim 2, wherein the coating is deposited on the medical device by dipping, spraying, molding, plasma deposition, or a combination thereof.

17. The method of claim 2, wherein the coating comprises a layer that is deposited on the medical device by plasma deposition.

18. The method of claim 2, wherein the coating is deposited by first depositing a base layer, selected for its ability to adhere to the medical device and then depositing thereon a top layer selected for its ability to bond to the base layer and avail the functional groups for attachment to the heparin.

19. The method of claim 2, wherein the functional groups comprise functional groups that are selected from a group consisting of amine groups, carboxyl groups, and a combination thereof.

20. The method of claim 2, wherein the bonding of the coating with heparin comprises ionic bonding.

* * * * *